(12) United States Patent
Limon

(10) Patent No.: US 9,921,094 B2
(45) Date of Patent: Mar. 20, 2018

(54) FLOW INDICATORS FOR SURGICAL INSTRUMENT REPROCESSING, AND RELATED SYSTEMS AND METHODS

(71) Applicant: INTUITIVE SURGICAL OPERATIONS, INC., Sunnyvale, CA (US)

(72) Inventor: Timothy Allen Limon, Cupertino, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1 day.

(21) Appl. No.: 14/871,395

(22) Filed: Sep. 30, 2015

(65) Prior Publication Data

US 2016/0135899 A1 May 19, 2016

Related U.S. Application Data

(60) Provisional application No. 62/078,057, filed on Nov. 11, 2014.

(51) Int. Cl.
*G01F 15/06* (2006.01)
*A61B 19/00* (2006.01)
(Continued)

(52) U.S. Cl.
CPC .............. *G01F 15/06* (2013.01); *A61B 19/34* (2013.01); *A61B 34/30* (2016.02); *A61B 90/70* (2016.02);
(Continued)

(58) Field of Classification Search
CPC ... A61B 90/00; A61B 90/70; A61B 2090/064; A61B 2090/702; A61B 2090/0807;
(Continued)

(56) References Cited

U.S. PATENT DOCUMENTS 2,780,199 A * 2/1957 Wittlin .................. G01P 13/008
116/276
3,857,277 A * 12/1974 Moore ...................... G01F 1/26
116/275
(Continued)

FOREIGN PATENT DOCUMENTS

GB 2205167 A * 11/1988 ............... G01F 1/28
WO WO 2006106632 A1 * 10/2006 ............ G01P 13/008
WO WO-2015023772 A1 2/2015

*Primary Examiner* — R. A. Smith
(74) *Attorney, Agent, or Firm* — Jones Robb, PLLC

(57) ABSTRACT

A surgical instrument flow indicator comprises a body defining a flow passage comprising an inlet and an outlet, wherein the inlet is configured to be fluidically coupled to a fluid supply source and wherein the outlet is configured to be fluidically coupled to the surgical instrument. The flow indicator further comprises a flow indication mechanism in flow communication with the flow passage, the flow indication mechanism being configured to transition from a first state to a second state in response to a threshold force exerted on the flow indication mechanism, wherein in the second state, the flow indication mechanism has an arrangement indicating to an observer that the flow indication mechanism transitioned from the first state to the second state.

22 Claims, 10 Drawing Sheets

(51) Int. Cl.
*G01L 1/00* (2006.01)
*H01H 35/24* (2006.01)
*A61B 90/70* (2016.01)
*A61B 34/30* (2016.01)
*G01C 19/00* (2013.01)
*G01P 13/00* (2006.01)
*A61B 90/00* (2016.01)

(52) U.S. Cl.
CPC ............... *G01C 19/00* (2013.01); *G01L 1/00* (2013.01); *G01P 13/0006* (2013.01); *G01P 13/0013* (2013.01); *H01H 35/24* (2013.01); *A61B 2019/343* (2013.01); *A61B 2019/346* (2013.01); *A61B 2090/064* (2016.02); *A61B 2090/0807* (2016.02)

(58) Field of Classification Search
CPC ...... G01F 15/06; G01F 15/065; G01F 15/066; G01P 13/00; G01P 13/0013; G01P 13/0026; G01P 13/008
USPC ............... 116/70, 264–276; 134/113; 73/744
See application file for complete search history.

(56) References Cited

U.S. PATENT DOCUMENTS

| | | | | |
|---|---|---|---|---|
| 4,416,033 A | * | 11/1983 | Specht | A47L 9/19 116/268 |
| 4,484,536 A | * | 11/1984 | Henocque et al. | G01P 13/0026 116/275 |
| 5,645,011 A | * | 7/1997 | Winkler et al. | B67D 7/56 116/264 |
| 5,761,069 A | * | 6/1998 | Weber et al. | G05B 19/41865 422/105 |
| 5,798,697 A | * | 8/1998 | Wiseman | G01P 13/0013 116/112 |
| 5,845,597 A | * | 12/1998 | Karpal | G01L 7/166 116/268 |
| 7,159,533 B1 | * | 1/2007 | Redd et al. | A61M 16/08 116/112 |
| 7,222,892 B2 | | 5/2007 | Guidetti | |
| 7,387,080 B2 | * | 6/2008 | Andronic | F15B 15/2807 116/267 |
| 7,467,890 B2 | * | 12/2008 | Patzek, IV | A61B 1/123 137/592 |
| 7,730,847 B1 | * | 6/2010 | Redd et al. | A61M 16/08 116/112 |
| 7,740,813 B2 | * | 6/2010 | Williams | A61B 1/123 134/104.1 |
| 7,891,311 B2 | * | 2/2011 | Logan et al. | A61M 5/14 116/270 |
| 8,241,271 B2 | * | 8/2012 | Millman et al. | A61M 1/0058 604/29 |
| 8,800,473 B1 | * | 8/2014 | DeVerse et al. | G01P 1/08 116/275 |
| 2013/0325031 A1 | | 12/2013 | Schena et al. | |
| 2013/0325033 A1 | | 12/2013 | Schena et al. | |

* cited by examiner

FLOW INDICATORS FOR SURGICAL INSTRUMENT REPROCESSING, AND RELATED SYSTEMS AND METHODS

CROSS-REFERENCE TO RELATED APPLICATIONS

This application claims priority to U.S. Provisional Application No. 62/078,057, filed Nov. 11, 2014, which is incorporated by reference herein in its entirety.

TECHNICAL FIELD

Aspects of the present disclosure relate to flow indicators for surgical instruments, which are useful for surgical instrument reprocessing. Aspects of the present disclosure further relate to surgical instruments and surgical instrument reprocessing machine washers including such flow indicators, and methods of cleaning surgical instruments.

INTRODUCTION

Remotely controlled surgical instruments, including surgical instruments operated at least in part with computer assistance, such as instruments operated with robotic "master-slave" and other remote telepresence technology, are often used in minimally invasive medical procedures. In teleoperated, computer-assisted surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Surgical instruments, including both manually operated and teleoperated surgical instruments, may be reprocessed after a surgical procedure so that the surgical instruments may be reused. A reprocessing procedure may include, for example both cleaning and decontamination of a surgical instrument, although processes of cleaning and decontamination may be performed in separate processes.

A goal of a reprocessing procedure is to remove as much residue from an instrument as possible, such as prior to decontamination. One way to clean an interior of an instrument (e.g., inside of a hollow shaft of an instrument) is to direct reprocessing fluid into the shaft interior, such as via a flushing process, so that the reprocessing fluid may carry residue away. In some situations, the reprocessing fluid flow may be reduced or blocked from the desired flow through the shaft and other interior positions of the instrument, which inhibits the cleaning process. Personnel performing a cleaning process are typically instructed to visually check that fluid is freely flowing through the instrument, such as when commencing the cleaning process and/or during the cleaning process, to ensure that the fluid is flowing. However, personnel may have difficultly observing whether flow is occurring during a cleaning process, such as when a surgical instrument is being cleaned inside an automated reprocessing unit that obstructs viewing of the instrument, when the flow of the fluid is obstructed by the instrument itself or other cleaning equipment, or it is otherwise difficult to view obstructions and/or the fluid flow within the instrument. Thus, while existing instrument reprocessing methods have been effective, a way to detect an insufficient (e.g., reduced or blocked) reprocessing fluid flow may be desired to further enhance cleaning effectiveness and provide additional assurance that surgical instruments have been cleaned as desired.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, the present disclosure contemplates a surgical instrument flow indicator comprises a body defining a flow passage comprising an inlet and an outlet, wherein the inlet is configured to be fluidically coupled to a fluid supply source and wherein the outlet is configured to be fluidically coupled to the surgical instrument. The flow indicator further comprises a flow indication mechanism in flow communication with the flow passage, the flow indication mechanism being configured to transition from a first state to a second state in response to a threshold force exerted on the flow indication mechanism, wherein in the second state, the flow indication mechanism has an arrangement indicating to an observer that the flow indication mechanism transitioned from the first state to the second state.

In accordance with another exemplary embodiment, the present disclosure contemplates a flow indicator for use during reprocessing of a surgical instrument that comprises a body defining a flow passage comprising an inlet and an outlet, wherein the inlet is configured to be fluidically coupled to a fluid supply source and wherein the outlet is configured to be fluidically coupled to the surgical instrument. The flow indicator further comprises a flow indication mechanism movable between a first position and a second position; a first retention mechanism disposed and configured to exert a first retention force on the flow indication mechanism to retain the flow indication mechanism in the first position, the first force being less than a threshold force acting in a direction to move the flow indication mechanism to a second position; and a second retention mechanism disposed and configured to exert a second retention force on the flow indication mechanism to retain the flow indication mechanism in the second position in the absence of another threshold force.

In yet another exemplary embodiment, the present disclosure contemplates a method comprising fluidically coupling a flow indicator between a reprocessing fluid supply source and a surgical instrument, and flushing portions of the surgical instrument by flowing a reprocessing fluid from the fluid supply source through the flow indicator. The flow indicator has a first state prior to the reprocessing fluid flowing through the flow indicator in a direction from the fluid supply source to the surgical instrument, and, on a condition that a sufficient backflow pressure of reprocessing fluid occurs during the flowing, the flow indicator transitions from the first state to a second state, the flow indicator remains in the second state after the transitioning and ceasing of the reprocessing procedure.

In another exemplary embodiment, the present disclosure contemplates a surgical instrument reprocessing system comprising a machine washer comprising a reprocessing fluid supply source and a flow indicator. The flow indicator comprises an inlet configured to be fluidically coupled to the machine washer reprocessing fluid supply source, an outlet configured to be fluidically coupled to a surgical instrument so as to flow reprocessing fluid from the machine washer reprocessing fluid supply source through an interior of a shaft of the surgical instrument, a passage extending from the inlet to the outlet; and a flow indication mechanism positioned in flow communication with the flow passage, the flow indication mechanism being configured to transition from a first state to a second state in response to a threshold force exerted on the flow indication mechanism. In the second state, the flow indication mechanism has an arrangement indicating to an observer that the flow indication mechanism transitioned from the first state to the second state.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
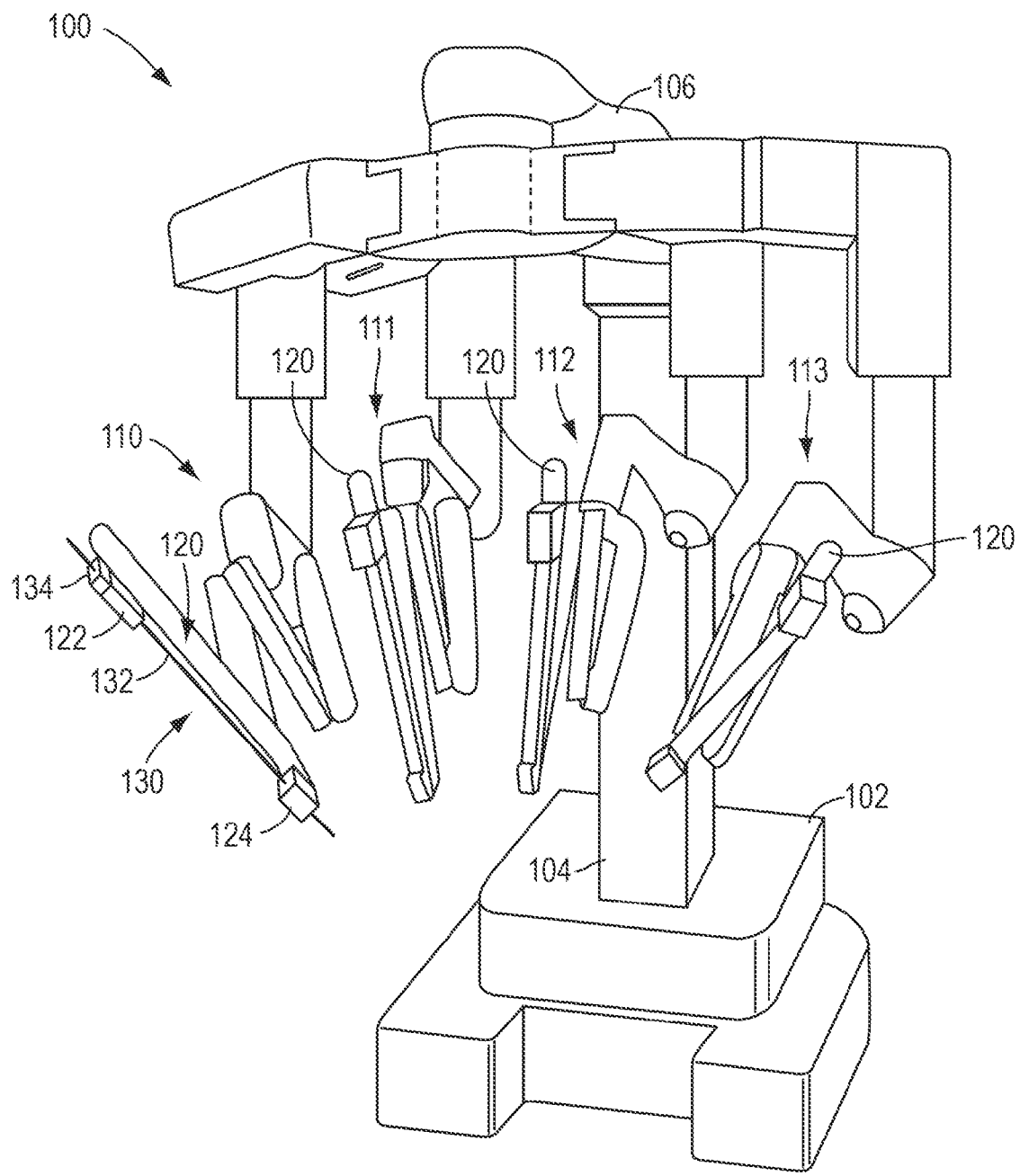
FIG. 1 is a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates flow indicators for surgical instruments that are configured to permit an observer to know whether or not a sufficient flow of reprocessing fluid through a surgical instrument has occurred during a reprocessing procedure, and more particularly during flushing. The flow indicator indicates, for example, that a back pressure caused by the reprocessing fluid occurred, such that it can be determined that the flow of reprocessing fluid during the cleaning was insufficient (e.g., was at or less than a threshold desired flow). To indicate the insufficient flow, the flow indicator includes a flow indication mechanism in fluidic communication with reprocessing fluid during a reprocessing procedure. In various exemplary embodiments, the flow indication mechanism is configured to transition from a first state prior to a reprocessing flushing procedure to a second state in response to either a sufficient flow of reprocessing flushing fluid flowing through the flow indicator or in response to a back pressure associated with a blockage or hindrance of flow through the instrument. In an exemplary embodiment, the flow indication mechanism has a first state prior to and during a reprocessing procedure having a sufficient flow of reprocessing fluid. The mechanism is then configured to transition to a second state when the flow of reprocessing fluid is at or below the threshold flow value during the reprocessing procedure. If the reprocessing fluid flow is insufficient during any portion of the flushing procedure, the mechanism can be configured to remain in the second state after the reprocessing procedure has ended and the flow of reprocessing fluid has stopped.

The flow indication mechanisms according to exemplary embodiments may provide feedback indicating that flow during the reprocessing was insufficient. For example, the flow indication mechanisms may be observable from an exterior of the flow indicator, at least in the second state, so that it is apparent to an individual looking at the flow indicator that the reprocessing fluid flow was not sufficient. In various exemplary embodiments, the transition of the flow indication mechanism from the first to the second state may be a change of position of the flow indication mechanism relative to the flow indicator. Other feedback also may be provided to permit an individual to determine from the flow indicator that insufficient flow occurred during the surgical instrument reprocessing procedure.

The present disclosure further contemplates methods relating to indicating that a reprocessing fluid flow through a surgical instrument was insufficient.

Referring now to FIG. 1, an exemplary embodiment of a patient side cart 100 of a computer-assisted, teleoperated surgical system is shown. A teleoperated surgical system further includes a surgeon console (not shown) for receiving input from a user to control instruments mounted at patient side cart 100. A teleoperated surgical system also can include an auxiliary equipment/vision cart (not shown), which optionally includes at least part of the system's computer control equipment and/or light source for endoscopic imaging control. Further, the exemplary embodiments described herein may be used, for example, with a da Vinci® Surgical System, such as the da Vinci Si® Surgical System, Single Site da Vinci® Surgical System, or a da Vinci® Xi Surgical System, available from Intuitive Surgical, Inc. of Sunnyvale, Calif. The various exemplary embodiments described herein also may be used with the exemplary embodiments of teleoperated surgical systems described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety.

Patient side cart 100 includes a base 102, a main column 104, and a main boom 106 connected to main column 104. Patient side cart 100 also includes a plurality of teleoperated manipulator arms 110, 111, 112, 113 (sometimes referred to as patient side manipulators (PSMs) or manipulators), which are each connected to main boom 106. Manipulator arms 110, 111, 112, 113 include an instrument mount portion 120 to which an instrument 130 is mounted, which in FIG. 1 is illustrated at manipulator arm 110. Portions of manipulator arms 110, 111, 112, 113 are manipulated during a surgical procedure according to commands provided by a user at the surgeon console. In an exemplary embodiment, signal(s) or input(s) transmitted from a surgeon console are transmitted to the control/vision cart, which interpret the input(s) and generate command(s) or output(s) to be transmitted to the patient side cart 100, for example through drive interface devices and ultimately to the surgical instrument transmission mechanism, to cause manipulation of an instrument 130 (only one such instrument being mounted at manipulation arm 110 in FIG. 1) and/or portions of manipulator arm 110 to which the instrument 130 is coupled at the patient side cart 100.

Instrument mount portion 120 includes an actuation interface assembly 122 and a cannula mount 124. A shaft 132 of instrument 130 extends through cannula mount 124 (and on to a surgery site during a surgical procedure). A force transmission mechanism 134 of instrument 130 is mechanically coupled with the actuation interface assembly 122. Cannula mount 124 is configured to hold a cannula (not shown in FIG. 1) through which shaft 132 of instrument 130 may extend to a surgery site during a surgical procedure. Actuation interface assembly 122 contains a variety of drives (e.g., servo-operated output drives) and other mechanisms that are controlled to respond to input commands at the surgeon console and transmit forces to the force transmission mechanism 134 to actuate instrument 130, as those skilled in the art are familiar with. For instance, the output drives of actuation interface assembly 122 directly engage with interface structures (not shown) of force transmission mechanism 134 and transmit forces to force transmission mechanism 134, as will be discussed further below.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) about a remote surgical site and/or its surroundings. In the exemplary embodiment of FIG. 1, a surgical instrument with an end effector or an imaging instrument may be attached to and used with any of manipulator arms 110, 111, 112, 113. However, the embodiments described herein are not limited to the exemplary embodiment of the patient side cart of FIG. 1 and various other teleoperated surgical system configurations, including patient side cart configurations, may be used with the exemplary embodiments described herein.

Figure 2:
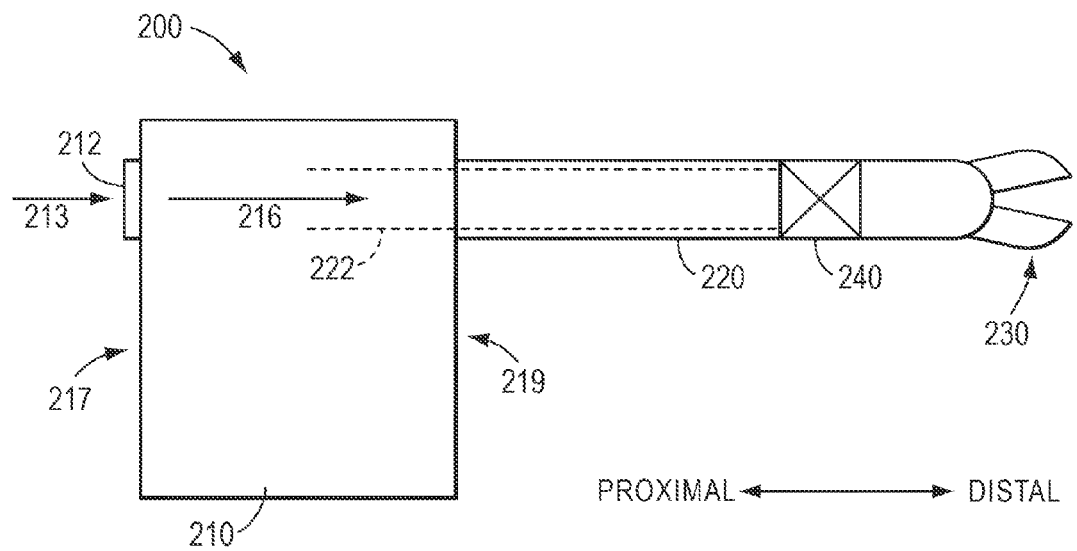
FIG. 2 is a side view of a surgical instrument, according to an exemplary embodiment.

FIG. 2 schematically depicts a side view of a surgical instrument 200, according to an exemplary embodiment, with relative proximal and distal directions of the instrument labeled. Surgical instrument 200 may be used in a teleoperated surgical system, such as by mounting surgical instrument 200 to any of manipulator arms 110-113 of patient side cart 100 of the exemplary embodiment of FIG. 1 (e.g., similar to instrument 130 in FIG. 1). According to an exemplary embodiment, surgical instrument 200 includes a force transmission mechanism 210 (e.g., as described with reference to force transmission mechanism 134 in FIG. 1), a shaft 220, and an end effector 230. The shaft 220 of surgical instrument 200 may include a wrist 240 for positioning end effector 230 relative to shaft 220 according to one or more degrees of freedom (e.g., pitch and/or yaw), or shaft 220 may lack a wrist.

To facilitate cleaning, surgical instrument 200 may include one or more openings for flowing a reprocessing fluid through an interior of the instrument. According to an exemplary embodiment, surgical instrument 200 includes a port 212 in the force transmission mechanism 210 to introduce reprocessing fluid to be flowed through surgical instrument 200 along the direction indicated by arrow 216 in FIG. 2. For example, reprocessing fluid 213 may be received by instrument 200 at port 212 to flow through force transmission mechanism 210, through shaft 220, and then exit instrument 200 via one or more holes or apertures in shaft and/or end effector 230. Surgical instruments of the present disclosure may be configured according to the various exemplary embodiments described in International Publication No. WO 2015/023772, entitled "Surgical Instruments and Methods of Cleaning Surgical Instruments," published Feb. 19, 2015, which is hereby incorporated by reference in its entirety. As indicated in the exemplary embodiment of FIG. 2, port 212 is located at a proximal end 217 of force transmission mechanism 210, but the present disclosure contemplates other numbers and positions of ports provided at the force transmission mechanism. Depending on the location of the port(s), those having ordinary skill in the art would understand that various fluid routing structures (not shown) may be located within the force transmission mechanism housing to direct the fluid into the surgical instrument shaft.

According to an exemplary embodiment, a flush tube 222 (shown with dashed lines in the exemplary embodiment of FIG. 2) may extend within force transmission mechanism 210 of instrument 200 through at least a portion of shaft 220. The flush tube 222 may be provided to direct reprocessing fluid supplied to the force transmission mechanism 210 via port 212 into an interior of shaft 220. The flush tube 222 may be directly connected to port 212 or may be indirectly connected such as via one or more fluid routing structures built into the force transmission mechanism connecting port 212 to the flush tube 222. The port 212 includes a fitting (e.g., a Luer type fitting) to connect the port 212 to a supply of reprocessing fluid.

As discussed above, a reprocessing procedure can include a cleaning process and a decontamination process (e.g., disinfecting process), either as separate processes or as parts of a single process. In the decontamination portion of instrument reprocessing, the cleaned instrument is typically either sterilized or disinfected. Sterilization destroys all microorganisms. Disinfection is less extreme than sterilization and destroys harmful microorganisms, or reduces the number of viable microorganisms to a level considered safe. In view of this, reprocessing fluid used in the various exemplary embodiments discussed herein may, for example, be at high pressure and/or high temperature to provide sterilization. Further, reprocessing fluid may include disinfecting substances, such as, for example, alcohol, phenolic compounds, and other substances used for disinfection and/or cleaning that are familiar to one of ordinary skill in the art. According to various exemplary embodiments, a temperature for reprocessing fluid flushing cycles range from 22° C. to 55° C., and fluid pressure ranges from 15 psi to 60 psi.

Figure 3:
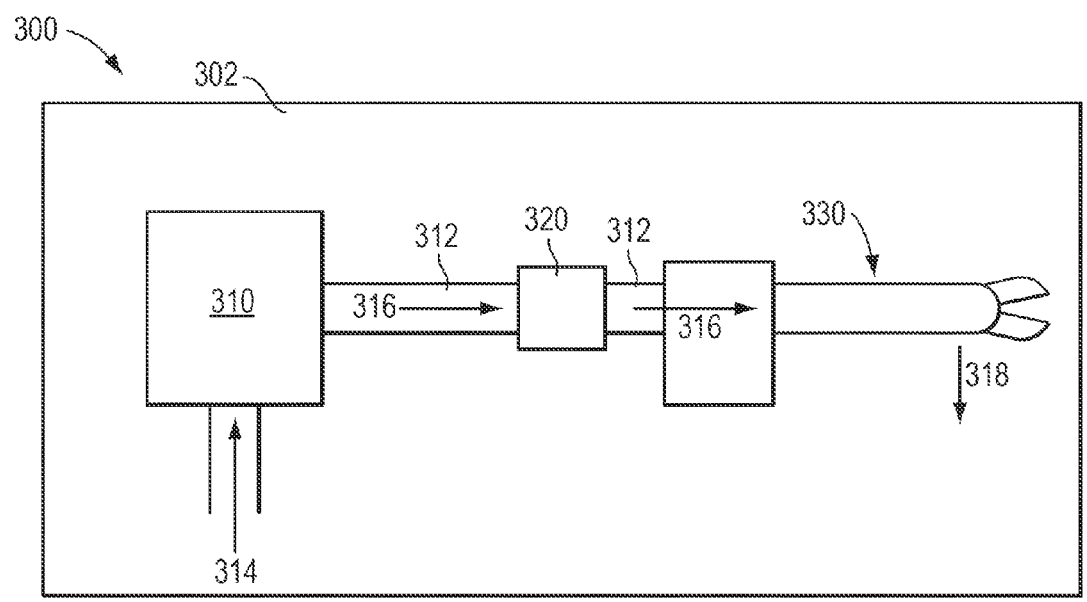
FIG. 3 is a schematic view of an automated reprocessing system for a surgical instrument, according to an exemplary embodiment.

Turning to FIG. 3, a side sectional view schematically depicts a reprocessing system for a surgical instrument, according to an exemplary embodiment. The reprocessing system depicted in the exemplary embodiment of FIG. 3 is an automated procedure using an automatic machine washer 300 that provides an enclosed area in which a surgical instrument 330 is reprocessed. The machine washer 300 includes a pump 310 that draws reprocessing fluid 314 from a source (not shown), which may be located within an interior 302 of machine washer 300 (e.g., a reservoir of reprocessing fluid located within the bottom of interior 302) or externally to machine washer 300. Examples of commercially available machine washers used for surgical instrument reprocessing, which those have ordinary skill in the art are familiar with and that may be used in conjunction with embodiments of the present disclosure include, but are not limited to, washer disinfectors commercially available from Belimed, such as model WD290; Getinge, such as model 88 Turbo; Medisafe, such as models Si PCF and Niagara; Miele, such as model PG8528; Steelco S.p.A, such as models DS 610 and DS 1000; and from Steris, such as the Vision models. Pump 310 is configured to be placed in flow communication with surgical instrument 330 to supply the reprocessing fluid 314 to surgical instrument 330, such as via tubes 312 and a flow indicator 320, which will be discussed in further detail below. For example, a tube 312 may be connected to port 212 discussed above with regard to the exemplary embodiment of FIG. 2. Therefore, pump 310 can supply reprocessing fluid along the direction indicated by arrow 316 through tubes 312 and flow indicator 320 to instrument 330, where the reprocessing fluid exits the instrument 330 (e.g., via openings (not shown) in instrument 330), as generally indicated by arrow 318. The reprocessing fluid may be collected by the washer for disposal or for further use. Machine washer 300 may further include one or more injectors (not shown) to spray the exterior of surgical instrument 330 with the reprocessing fluid during a reprocessing procedure. Although one surgical instrument 330 is depicted in FIG. 3 as being reprocessed by washer 300, the present disclosure contemplates more than one surgical instrument being disposed in the machine washer 300 for simultaneous reprocessing, for example in a manner similar to loading a household dishwasher. During a reprocessing procedure, instrument 330 is connected to the pump 310 (e.g., via tubes 312 and flow indicator 320) within the interior 302 of washer 300 and the machine washer 300 remains closed during the duration of the reprocessing procedure. Persons having ordinary skill in the art are generally familiar with the use of the type of automatic machine washers used for reprocessing of surgical instruments described above.

Figure 4:
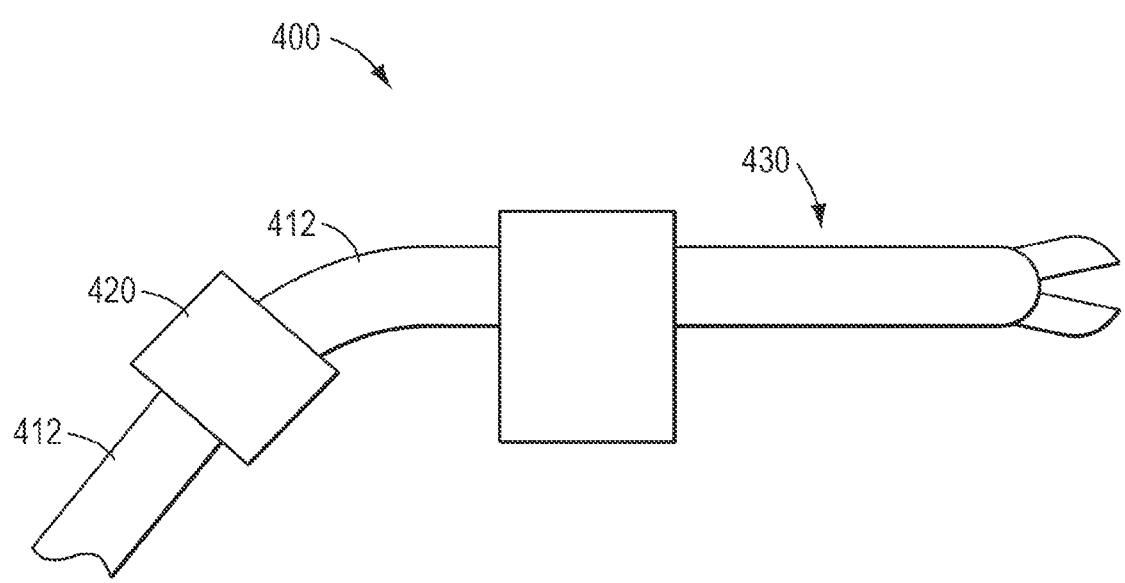
FIG. 4 is a schematic view of a manual reprocessing system for a surgical instrument, according to an exemplary embodiment.

The present disclosure also contemplates non-automated reprocessing procedures. FIG. 4 schematically depicts an exemplary embodiment of a manual reprocessing system 400 in which a surgical instrument 430 is reprocessed by connecting tubes 412 supplying reprocessing fluid, e.g., from a fluid source (not shown), to the surgical instrument 430 via a port (e.g., port 212) and flushing the instrument manually, such as by a hand-held spray device or via connection to a faucet (not shown). A flow indicator 420 may be connected to the tubes 412 so that the reprocessing fluid flows through the flow indicator 420, as will be discussed below.

Those having ordinary skill in the art would appreciate that the tubes 312, 412 may be provided separately from or as integrated structures with the flow indicators. Moreover, in an exemplary embodiment, it is contemplated to include a flow indicator as an integral structure with the machine washer.

Minimally invasive surgical instruments, whether a tele-operated surgical instrument or a manually operated instrument, have complex designs, with various components (e.g., cables, rods, hypotubes, tubes, or other components) extending through an interior of the instrument, such as within an interior of the hollow shaft of the instrument. Such components may lead to a reduction in the flow of reprocessing fluid, or a blockage thereof, through the instrument. For example, excess residue may impair or block flow of reprocessing fluid, or a flush tube (e.g., flush tube 222 of FIG. 2) through which the reprocessing fluid flows can become compressed or kinked. For instance, the instrument shaft may be rolled, which may lead to components that extend along an exterior of a flush tube (e.g., cables, rods, etc.) being twisted about the flush tube and compressing the flush tube. Any of these, as well as other causes that lead to a reduction or blockage of reprocessing fluid flow may negatively impact the reprocessing of the instrument for reuse. However, because often the causes of a reduction or blockage of reprocessing fluid flow are located in the interior of an instrument, it is difficult for reprocessing personnel to observe or otherwise detect when such reduction or blockage of reprocessing fluid flow occurs. In addition, when a machine washer (e.g., washer 300 in FIG. 2) is used to reprocess an instrument, the instrument is located within the machine washer and is difficult to view. Therefore, reprocessing personnel may not discover that an instrument has not been properly reprocessed due to insufficient reprocessing fluid flow.

Accordingly, the present disclosure contemplates the use of relatively inexpensive and easy to use devices that are configured to indicate the sufficiency of a flow of reprocessing fluid through an instrument so that it can be determined whether or not there may have been insufficient fluid flow through the instrument to flush the instrument during a reprocessing procedure.

The present disclosure contemplates flow indicators that indicate that an insufficient reprocessing fluid flow has occurred during a reprocessing fluid flushing of the instrument. Such insufficient fluid flow (e.g., a flow that is at or less than a threshold) can be a result of a blockage or impediment in the normal flow direction of the reprocessing fluid flow. According to an exemplary embodiment, when an instrument is connected to a source of reprocessing fluid, which is provided at a known and generally constant pressure range (e.g., during a manual or automated reprocessing flushing procedure), and a blockage or impediment in flow of the reprocessing fluid occurs, a back pressure will occur, such as within a tube supplying the reprocessing fluid to the shaft of the instrument. Therefore, flow indicators in accordance with various exemplary embodiments described herein may be configured to indicate an insufficient flow of reprocessing fluid when the flow of reprocessing fluid is at or below a threshold flow rate that is less than a first flow rate that occurs when the reprocessing fluid freely flows through the surgical instrument as desired to flush out the instrument during reprocessing. For example, a desired flow of reprocessing fluid can occur when the surgical instrument lacks any obstructions or other unexpected impediments to fluid flow that may cause an impeded or blocked flow of the reprocessing fluid in the normal direction of flow to reprocess the instrument.

In various exemplary embodiments, flow indicators are configured to detect when back pressure at or above a threshold level occurs and provide an indication that insufficient flow of reprocessing fluid has occurred or is occurring. Thus, the flow indicator may be used to determine if sufficient reprocessing fluid flow is occurring when initially commencing a reprocessing procedure, or may be used after completion of a reprocessing flushing procedure to determine whether sufficient flow occurred during a reprocessing flushing procedure. According to an exemplary embodiment, the indication may be visual, such as, for example, via a change in position of at least a portion of the flow indicator and/or other visual indication familiar to one of ordinary skill in the art. The flow indicator is positioned between a source of reprocessing fluid and an instrument, such as between a pump and an instrument, as indicated in the exemplary embodiment FIG. 3, whether during an automated reprocessing procedure or during a manual reprocessing procedure. As a result, reprocessing fluid flows through the flow indicator and is supplied to the instrument during a reprocessing procedure, with the flow indicator providing an indication as to whether or not the flow of fluid was sufficient (or alternatively was not impeded or blocked) during reprocessing.

Figure 5:
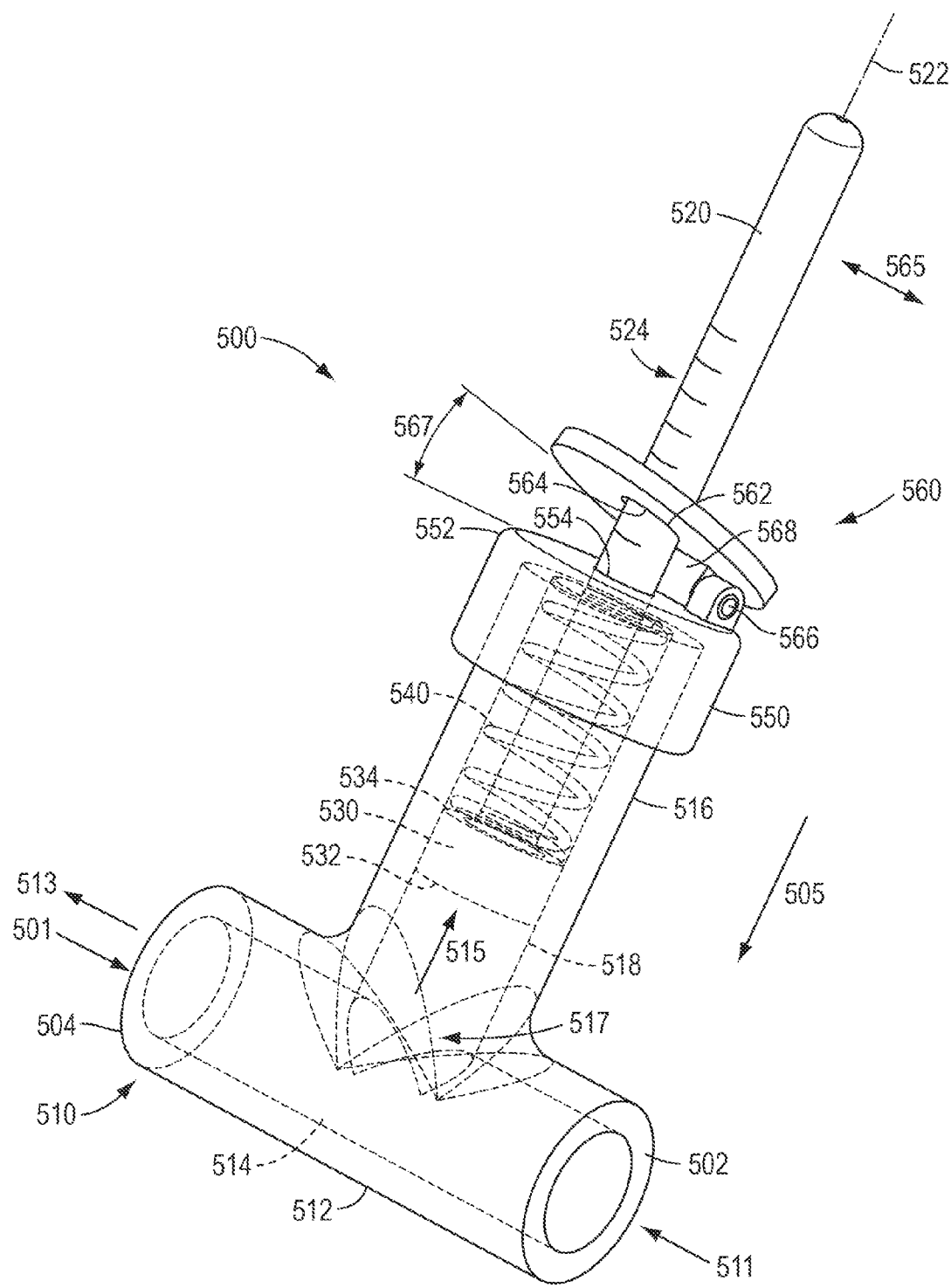
FIG. 5 is a perspective view of a flow indicator, according to an exemplary embodiment.

FIG. 5 illustrates one exemplary embodiment of a flow indicator in accordance with the present disclosure. Flow indicator 500 includes a generally t-shaped body 510 including a tube portion 512 having an open passage 514 through which reprocessing fluid may flow. For example, an open first end 502 of the tube portion 512 can be connected to a reprocessing fluid source (e.g., via a tube or other connection mechanism connected to first end 502) and an open second end 504 of the tube portion 512 can be connected to a surgical instrument (e.g., via a tube or other connection mechanism connected to second end 504), similar to the arrangement described above with regard to the exemplary embodiments of FIGS. 3 and 4. Therefore, during a reprocessing procedure, reprocessing fluid may flow into first end 502 of channel portion 512, such as along the direction indicated by arrow 511, through passage 514, and out of second end 504, such as along the direction indicated by arrow 513, to an instrument (not shown) to be reprocessed. For example, second end 504 can be configured to attach to a port for flushing a surgical instrument, such as port 212 in the exemplary embodiment of FIG. 2, or an intermediate tube, such as tubes 312, 412, connected to port 212.

Flow indicator 500 is configured to indicate the occurrence of an impeded or blocked reprocessing fluid along the directions 511, 513. To do so, flow indicator 500 is configured to detect a back pressure in the flow of the reprocessing fluid. More specifically, body 510 of flow indicator 500 further includes a second tube portion 516 connected at a junction to tube portion 512 between the ends 502, 504 of tube portion 512. Second tube portion 516 has a back flow passage 518 fluidically connected to passage 514 of tube portion 512 through an opening 517. As indicated in the exemplary embodiment of FIG. 5, back flow passage 518 may be substantially perpendicular to passage 514, although the present disclosure contemplates other angles between passage 514 and back flow passage 518. As will be explained in further detail below, back flow passage 518 also is blocked so that fluid cannot flow through the passage 518 to exit the body 510.

During normal operation of a reprocessing procedure, e.g., in which no back flow pressure or substantially little back flow pressure occurs, reprocessing fluid flows through passage 514 from first end 502 to second end 504 in direction 511 exiting at 513 with little or no reprocessing fluid entering back flow passage 518. However, the occurrence of a blockage of the flow in the instrument during fluid continuing to flow in directions 511, 513 causes a back pressure of reprocessing fluid to occur, resulting in a pressure build up in direction 501. In this way, the reprocessing fluid flows back into second end 504, along passage 514, and into back flow passage 518 along the direction indicated by arrow 515. The back pressure builds in back flow passage 518 because of the fluid flow continuing in the direction 511 to prevent the flow 501 from flowing back out through open end 502.

Flow indicator 500 includes a mechanism configured to be actuated by a back flow pressure acting upon flow indicator 500. According to an exemplary embodiment, the mechanism is fluidically connected to, or located within, flow passage 518. Therefore, when sufficient back pressure occurs and reprocessing fluid is forced into the back flow passage 518 of flow tube 516, the mechanism is actuated by the fluid flow 518 to indicate that an insufficient flow (e.g., a flow that is at or less than a threshold value) of reprocessing fluid has occurred through the instrument during the reprocessing flushing procedure. In this and other exemplary embodiments described herein, the threshold flow rate value may range from 200 milliliters per minute (ml/min) to 1100 ml/min at pressures of 15 pounds per square inch (psi) to 60 psi. In other words, flow rates at or above the aforementioned range can be considered as sufficient flow for a reprocessing flushing procedure.

According to an exemplary embodiment, the back flow pressure indication mechanism includes a piston assembly including shaft 520 and, a piston head 530, a first biasing device 540, and a second biasing device 560, which is an anti-backlash mechanism in the exemplary embodiment of FIG. 5. Piston head 530 is connected to shaft 520, either as a second piece internally joined to shaft 520 or as second portion of a single piece construction including shaft 520 and piston head 530. In FIG. 5, the piston assembly is located within back flow passage 518 of second tube portion 516, with the piston head 530 facing opening 517, and the shaft 520 extending from the piston head 530 in a direction toward the end 552 of tube portion 516 opposite opening 517. The first biasing device 540 is configured to hold the piston assembly in a first state corresponding to a non-actuated position, such as by exerting a force to move piston head 530 along the direction indicated by arrow 505 in FIG. 5. First biasing device 540 may be, for example, a compression spring, such as, for example, a helical compression spring, or other type of biasing device used to force piston head 530 along direction 505. To exert the force on piston head 530, first biasing device 540 is compressed between an inner surface of the end 552 of flow tube 516 and a surface 534 of piston 530. For example, the first biasing device 540 may be attached or otherwise secured in place at its ends to the surfaces. Thus, when first biasing device 540 is a compression spring, the compression spring acts against the inner surface of the closed end 552 and presses against the top surface 534 of piston head 530 to force the piston assembly downward along direction 505.

Shaft 520 extends past the end 552 of the second tube portion 516 to a location exterior to body 510. For example, shaft 520 extends through an opening 554 in the end 552 of flow tube 516. Opening 554 includes a sealing member, such as for example an O-ring or other sealing member, that engages and surrounds shaft 520 to fluidically seal the passage 518 between the opening 554 and the shaft 520, according to an exemplary embodiment. The end 552 may be formed by the flow tube 516 or, as illustrated in FIG. 5, by a flange cap 550 connected to the flow tube 516.

If, as described above, reprocessing fluid is forced into back flow passage 518, the reprocessing fluid acts against surface 532 of piston head 530. If the fluid flow 515 acting on the piston head 530 is sufficient, it will overcome the force exerted upon piston head 530 by first biasing device 540. Thus, the pressure from backflow of reprocessing fluid can overcome the force exerted by the first biasing device 540, causing the piston assembly, including both piston head 530 and shaft 520, to move in the direction indicated by arrow 515 in FIG. 5.

The flow indicator 500 is further configured such that the resulting movement of shaft 520 through aperture 554 and further out of flow tube 516 provides an indication that the back pressure and an insufficient flow of reprocessing fluid through the instrument has occurred. For example, a length of the shaft 520 past aperture 554 may be used to provide feedback of the occurrence and level of the back pressure. According to an exemplary embodiment, shaft 520 includes indicia 524, such as one or more marks (e.g., paint, groove, embossment, or other method of making a mark on shaft 520) along a length of shaft 520 that can be observed by an individual (e.g., reprocessing personnel) to determine how far shaft 520 has been extended out of flow tube 516, relative to an initial position prior to the reprocessing flushing procedure. For example, the relative position of the shaft and the end 552 of the tube portion 516 may be observed, and the indicia 524 may be compared to a point of reference, such as, for example, end 552 or a portion of anti-backlash mechanism 560, described further below. The indicia may be configured to indicate a magnitude of the back pressure, and thus a reduction in flow of reprocessing fluid, and/or to determine whether impedance or blockage of reprocessing fluid flow has occurred, by comparing the relative position of the indicia 524 to the point of reference. Thus, positions of the indicia 524 may correspond to predetermined lengths of the shaft 520 extending outside of flow tube 516, which in turn correspond to a flow pressure indicating impeded or blocked flow of reprocessing fluid. As a result, the position of shaft 520 is configured to indicate that reprocessing fluid flow may not have been sufficient through the instrument, and flushing the instrument may not have occurred properly.

Although a back pressure may cause piston head 530 and shaft 520 to move and indicate the back pressure, the back pressure may not be constant and/or may not exist when reprocessing personnel check the flow indicator 500 to see if back pressure occurred. For example, in an automated reprocessing procedure, such as within machine washer 300 of FIG. 3, the pressure provided by a reprocessing fluid source may be shut off, causing the back pressure to cease prior to the flow indicator 500 being accessed by opening the washer 300. To address this and provide reprocessing personnel and/or other individuals with feedback that the back pressure occurred, anti-backlash mechanism 560 is configured to minimize or prevent movement of shaft 520 back into flow tube 516 along direction 505 in FIG. 5 after shaft 520 has been extended out of flow tube 516 due to a back pressure. In other words, anti-backlash mechanism 560 acts to minimize or prevent retraction of the shaft 520 toward passage 514 so as to allow for observation of the extent that shaft 520 has extended out of flow tube 516 even after the completion of flushing and reprocessing of the instrument.

According to an exemplary embodiment, anti-backlash mechanism 560 includes a plate 562 having an aperture 564 through which shaft 520 extends. A hinge 566 connects plate 562 to the body 510. In particular, hinge 566 connects the plate 562 at a side of the plate to an edge of the end 552, for example either to the cap 550 (shown in FIG. 5) or to the tube portion 516 if there is no cap (not shown). In the exemplary embodiment of FIG. 5, the plate 562 is held at an angle 567 relative to the plane of the end 552 of tube portion 516. Hinge 566 may include a biasing device 568, such as a coil spring wrapped about a pin of the hinge 566, which exerts a force to hold plate at angle 567. In an exemplary embodiment, angle 567 can range from 10° to 35°, but other angles are also considered within the scope of the present disclosure. Further, plate aperture 564 is located in plate 562 so that aperture 564 is slightly radially offset from shaft 520 along a transverse direction 565 relative to longitudinal axis 522 of shaft 520. In this arrangement, the perimeter of aperture 564 and the perimeter of shaft 520 at the location where the shaft 520 extends through the aperture do not coincide exactly, but rather are slightly radially offset from each other. Due to the radial offset and/or angle of plate aperture 564 relative to shaft 520, surface of plate 562 defining aperture 564 contacts at least a portion of an outer circumferential surface of shaft 522 in a manner that permits shaft 520 to slide through aperture 564 out of flow tube 516 along direction 515 in FIG. 5. However, movement of shaft 520 back into flow tube 516 along direction 505 in FIG. 5 is minimized or prevented due to friction between plate 562 and shaft 520.

The shaft and the plate may be made of a variety of materials, including a variety of plastic or metal materials. According to an exemplary embodiment, a material of shaft 520 may be softer than the material of plate 562 to facilitate slight deformation of shaft 520 to allow the surface of the plate 562 surrounding aperture 564 to grip the shaft 520, which further minimizes or prevents movement of shaft 520 along direction 505. Further, persons skilled in the art will appreciate various other mechanisms that can be used to allow an object to move in one direction but prevent the object from moving in an opposite direction, and which would be suitable for use in aspects of the various exemplary embodiments described herein.

Flow indicators in various exemplary embodiments are resettable after use in a reprocessing procedure. For example, flow indicator 500 may be reset, by manually adjusting plate 562 to permit shaft 520 to slide through aperture 564. By manually moving the plate 562 to align the aperture 564 and shaft 520, the frictional engagement between the plate 562 and the shaft 520 is released. More specifically, plate 562 can be manually pivoted about hinge 566 to reduce angle 567. Upon releasing the frictional grip of plate 562 on the shaft 520, first biasing device 540 is free to return to its elongated, uncompressed initial position in which it exerts a force on piston 530 to push piston 530 downward along direction 505 in FIG. 5, thereby pulling shaft 520 downward, and resetting flow indicator 500.

Figure 6:
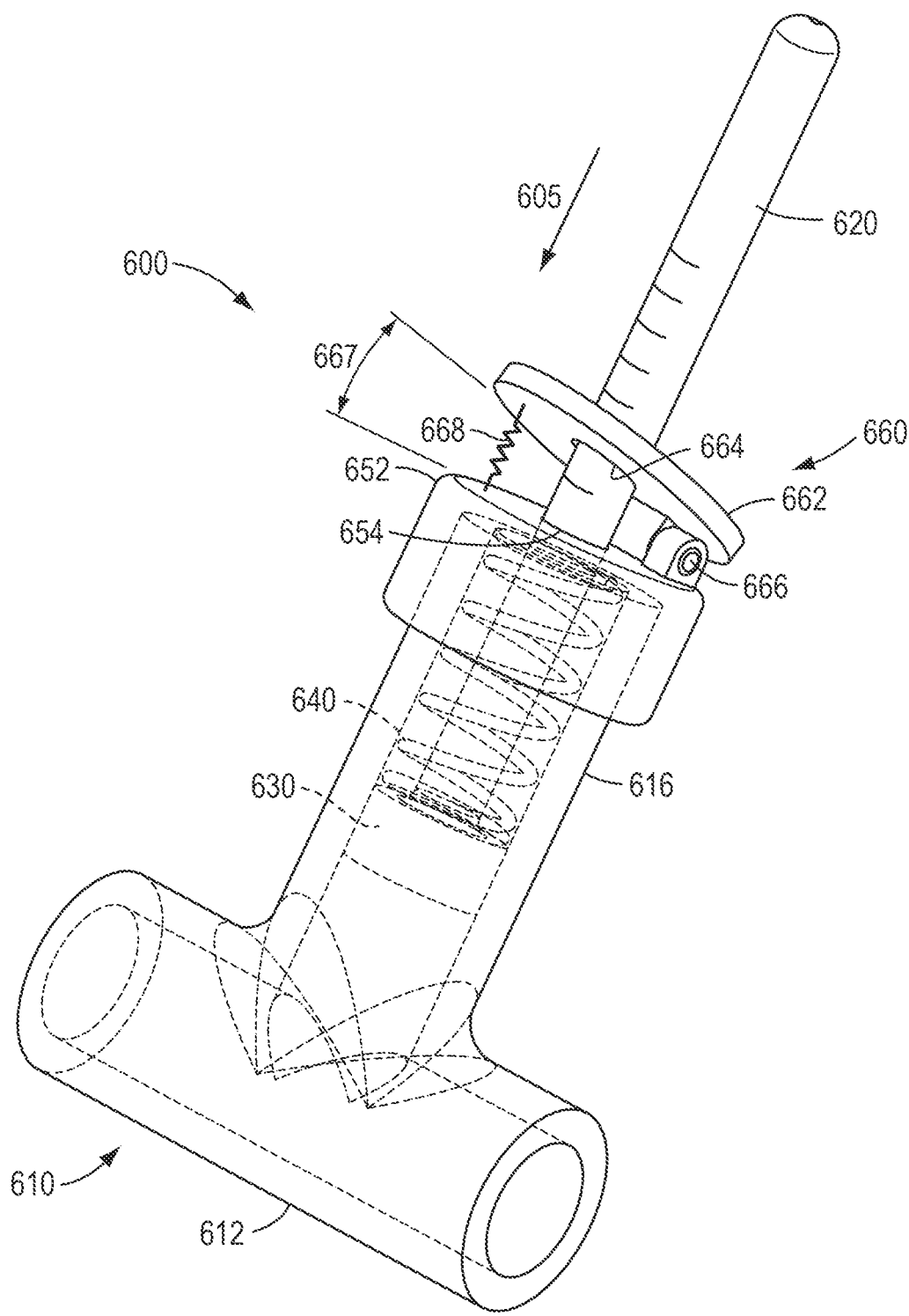
FIG. 6 is a perspective view of a flow indicator, according to another exemplary embodiment.

The present disclosure contemplates other configurations of a flow indicator for use in reprocessing surgical instruments. FIG. 6 depicts an exemplary embodiment of a flow indicator 600 having a structure similar to flow indicator 500 of the exemplary embodiment of FIG. 5, in that flow indicator 600 includes a body 610 having a first tube portion 612 and a second tube portion 616 which meet at a junction, a piston assembly, structured like piston assembly of FIG. 5 within tube portion 616 and having a piston head 630 connected to a shaft 620. As with the flow indicator 500, the flow indicator 600 also includes a first biasing device 640 that urges the piston head 630 to a first state in a non-actuated position, and an anti-backlash mechanism 660, as discussed above with regard to the exemplary embodiment of FIG. 5. Shaft 620 extends out of flow tube 616 through opening 654 in end 652 and through an aperture 664 of a plate 662 of anti-backlash mechanism 600, which is connected to the rest of flow indicator 600 via a hinge 666, in a manner like that discussed above with regard to the exemplary embodiment of FIG. 5. Thus, flow indicator 600 is structured and functions in much the same way as flow indicator 500 of FIG. 5, except that anti-backlash mechanism 660 includes a biasing device 668 connecting flow tube 616 and plate 662, rather than a biasing device provided at the hinge 666. For example, as shown in FIG. 6, the biasing device 668 may be a coil spring or other type of biasing device that applies a tensile force between the end 652 of flow tube 616 and plate 662. As the shaft 620 extends out of the tube portion 616, for example when a back pressure is acting on the piston inside the tube portion 616, anti-backlash mechanism 660 is configured to maintain plate 662 at an angle 667 relative to the end 652 by the spring 668 pulling the plate downward such that friction between the plate 662 and the shaft 620 maintain the plate 662 in an angled position once the shaft 620 has moved out of the tube portion 616 due to pressure from fluid flow. However, the plate 662 is able to be manually moved downward toward closed end 652 by pivoting plate 662 about hinge 666 to reduce angle 667. Manually moving the plate 662 toward the closed position returns biasing device 668 to a low energy relatively compressed state and resets flow indicator 600 for another use during a reprocessing procedure.

Figure 7:
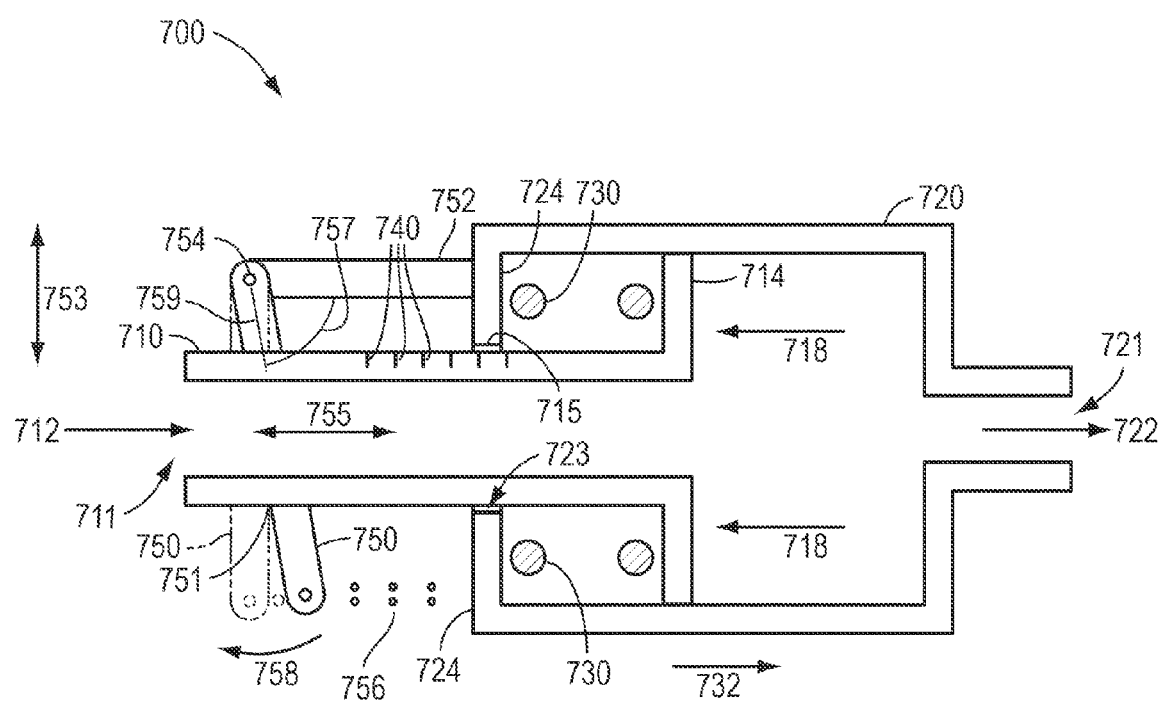
FIG. 7 is a side sectional view of a flow indicator, according to another exemplary embodiment.

Turning to FIG. 7, a sectional view of another exemplary embodiment of a flow indicator is depicted. Flow indicator 700 includes a first tube section 710 and a second tube section 720, with at least a portion of first tube section 710 being received within second tube section 720 in a telescoping type arrangement. A flange 714 disposed at an end of first tube section 710 is located within second tube section 720, as depicted in the exemplary embodiment of FIG. 7, to stop first tube section 710 from being uncoupled from second tube section 720. A sealing member 715, such as an o-ring, gasket or the like, provides sealing engagement between the first tube section 710 and the second tube section 720.

To perform a reprocessing flushing procedure, flow indicator 700 is fluidically connected to a source of reprocessing fluid at an inlet 711 of first tube section 710 (e.g., via a tube) and is fluidically connected to a surgical instrument at an outlet 721 of second tube section 720 (e.g., via a tube). Reprocessing fluid can then flow from the fluid source (not shown in FIG. 7) through flow indicator 700 along the flow directions indicated by arrows 712, 722, into first tube section 710 and out of second tube section 720 to the surgical instrument, as described above.

The tube section 710, with its associated flange 714, is configured to act like a piston that is moved when a back pressure occurs in the reprocessing fluid flowing through flow indicator 700. More specifically, the flange 714 forms a piston head upon which a back pressure of reprocessing fluid as indicated at 718 can exert a force to move the tube section 710 in a direction away and out from the tube section 720. In a manner similar to the piston assemblies described above, flow indicator 700 includes a biasing device 730 (shown in cross-section) disposed between the flange 714 of first tube section 710 and the inner, reprocessing fluid inflow end 724 of second tube section 720. The biasing device 730 may be, for example, a coil spring or other type of biasing device configured to have an uncompressed, low energy state that spaces the flange 714 from the inner, inflow end 724. When a back pressure occurs in the reprocessing fluid flow, the back pressure acts along the direction indicated by arrows 718 in FIG. 7 against flange 714 of first tube section 710, causing first tube section 710 to be moved against the force exerted by biasing device 730, for example, by compressing the biasing device when in the form of a coil spring. Thus, first tube section 710 can act as a piston that is moved by the back pressure of the reprocessing fluid.

Flow indicator 700 is configured to indicate that a sufficient back pressure has occurred and that a flow of reprocessing fluid was thus insufficient through the instrument shaft (e.g., a flow that is at or less than a threshold value) during a reprocessing flushing procedure. For example, in a manner similar to that described with respect to the embodiment of FIG. 5, first tube section 710 includes indicia 740 such as one or more marks (e.g., paint, groove, embossment, or other method of making a mark on an outer surface of first tube section 710) that can be observed to determine how far first tube section 710 has been extended out of the end 724 of second tube section 720. An exterior portion of the first tube section 710 includes indicia 740 at a location proximate end 724 such that the indicia 740 may be exposed upon extension of the first tube section 710 out of second tube section 720 during movement of the first tube section 710 in response to the back flow 718. The relative position of the indicia 740 may be compared to a point of reference, such as, for example, aperture 723 or a portion of second tube section 720 (e.g., end 724). The indicia can indicate a relative magnitude of the back pressure, and thus a reduction in flow of reprocessing fluid, and/or to determine whether reprocessing fluid flow was impeded or blocked during a reprocessing flushing procedure, by comparing the relative position of the indicia 740 to the point of reference. As also described with respect to FIG. 5, other mechanisms for providing feedback to an individual regarding whether a flow through the surgical instrument during reprocessing was insufficient during the reprocessing are envisioned and considered within the scope of the present disclosure.

Flow indicator 700 also includes an anti-backlash mechanism to minimize or prevent the retraction of first tube section 710 back into second tube section 720 after a back pressure has ceased. Similar to the embodiments of FIGS. 5 and 6, the anti-backlash mechanism includes a plate 750 attached to the end 724 of the second tube section 720 by a link 752. The plate 750 is pivotably coupled (e.g., via a pin 754) to the link 752. The anti-backlash mechanism may function in a similar manner to the anti-backlash mechanisms of the exemplary embodiments of FIGS. 5 and 6. For example, the tube section 710 extends through an aperture 751 of plate 750. The plate 750 may be biased at an angled position relative to first tube section 710. Aperture 751 is radially offset from first tube section 710 (e.g., along a transverse direction 753 relative to longitudinal axis 755 of first tube section 710) so that in the biased position, the surface of the plate 750 surrounding the aperture 751 frictionally engages the outer surface of the first tube section 710 in a manner that inhibits the first tube section 710 from sliding through aperture 751 and thus retracting back into second tube section 720. However, as sufficient back pressure is created along direction 718 to overcome the force of the biasing device 730, movement of the first tube section 710 tends to pivot the plate 750 into the dashed line position illustrated so as to better align the aperture 751 and the first tube section 710, thereby permitting movement and extension of the first tube section 710 out of the second tube section 720. The frictional engagement force between the plate 750 and the first tube section 710 is greater than the force exerted by biasing device 730 so as to hold the first tube section 710 in its most extended position out of the second tube section 720 and prevent retraction of the first tube section 710 back into second tube section 720 in the absence of the back flow pressure.

As above, in various exemplary embodiments, the first tube section and the plate may be made of a variety of materials, including a variety of plastic or metal materials. According to an exemplary embodiment, a material of first tube section 710 may be softer than the material of plate 750 to facilitate slight deformation of first tube section 710 to allow the surface of the plate 750 surrounding aperture 751 to grip the first tube section 710, which further minimizes or prevents retraction of the first tube section 710 back into the second tube section 720.

Further, persons skilled in the art will appreciate various other mechanisms that can be used to allow an object to move in one direction but prevent the object from moving in an opposite direction, and which would be suitable for use in aspects of the various exemplary embodiments described herein.

In operation to indicate insufficient fluid flow during a reprocessing flushing procedure, when a sufficient back pressure occurs and first tube section 710 is moved so as to be further extended out of the second tube section 720, generally in the direction indicated by the arrows 718, as described above. Plate 750 is urged along the same direction due to its engagement with first tube section 710. As the plate 750 moves, it pivots about pin 754 along the directions indicated by arrows 758 in FIG. 7 and as depicted in the dashed lines. In this position, as described above, the aperture 751 is aligned with the first tube section 710 to permit first tube section 710 to slide through the aperture 751 and extend further out of second tube section 720. A tension spring 756 (shown in cross-section) or other biasing device that in its normal, low energy state urges the free end of plate 750 toward flange 724 attempts to return from its elongated state toward its initial low energy state so as to bias plate 750 at the angle 757 as shown in FIG. 7. However, due to the radially offset aperture 751, as the spring 756 attempts to return to its initial state, the plate 750 frictionally engages with the outer surface of the first tube section 710.

When it is desired to reset the flow indicator 700, for example, after the reprocessing procedure so as to use the flow indicator for another reprocessing procedure, the first tube section 710 may be returned to an initial position within second tube section 720 by manually adjusting (pivoting) the plate 750 to permit first tube section 710 to slide through aperture 751 of plate 750 to return to the first tube section 710 and the anti-backlash mechanism to their respective initial positions.

As with the other exemplary embodiments, other configurations for backlash mechanisms are envisioned as within the scope of the present disclosure, with the arrangements described and shown being non-limiting and exemplary only.

Figure 8:
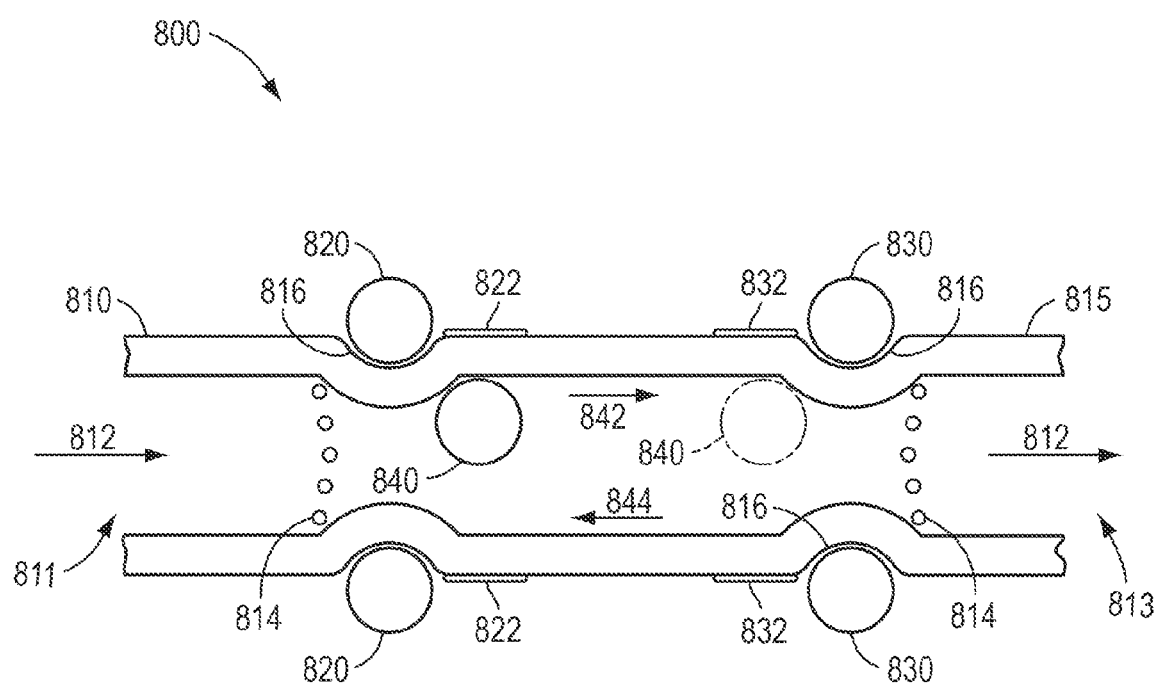
FIG. 8 is a sectional view of a flow indicator, according to another exemplary embodiment.

The present disclosure also contemplates flow indicators that rely on other structures and biasing mechanism types for their operation. FIG. 8 depicts a sectional view of another exemplary embodiment of a flow indicator 800 to be used in a reprocessing flushing procedure, wherein the flow indicator 800 relies on magnetic forces rather than spring forces. Flow indicator 800 includes a tube 810 configured to be fluidically coupled to a source of reprocessing fluid, (not shown) at inlet 811, and to a surgical instrument at outlet 813, so that reprocessing fluid flows through tube 810 during a reprocessing procedure along a direction indicated by arrows 812 in FIG. 8. As above, intermediate tubes may be used to fluidically couple the flow indicator to the fluid supply source and/or the surgical instrument.

In the embodiment of FIG. 8, a flow indication member 840 is located within tube 810 and subjected to the flow of reprocessing fluid through tube 810. Flow indication member 840 includes a magnetic element (e.g., an element made of a material capable of being magnetized or attracted by a magnet) having the shape of a sphere although flow indication member 840 may have other shapes, such as, for example, a solid cylinder having a longitudinal axis aligned along direction 812, a hollow cylinder having a longitudinal axis aligned along direction 812, or other shape. Flow member 840 may be, for example, a magnet material encased in plastic. The plastic encasing may be provided to minimize or prevent corrosion of flow indication member 840 in the reprocessing fluid, which may be alkaline in nature. Flow indication member 840 is sized so as not to obstruct the flow of reprocessing fluid through tube 810. According to an exemplary embodiment, flow indication member 840 may have a width or diameter that ranges from, for example, about 50% to about 70% of the inner diameter of tube 810. According to another exemplary embodiment, flow indication member 840 includes a magnet (e.g., a permanent magnet), such as, for example, a metal magnet encased in plastic.

Flow indicator 800 further includes a first magnet 820 and a second magnet 830 (each shown in cross-section in FIG. 8) spaced apart from one another along tube 810. The first magnet 820 is positioned upstream of the second magnet 830 in direction of fluid flow during a normal reprocessing flushing procedure, i.e., in direction 812. Suitable materials that can be used to make the magnets, as well as the magnets of other embodiments disclosed herein, include, but are not limited to, for example, alloys containing iron, nickel, or cobalt, or combinations thereof. In the exemplary embodiment of FIG. 8, the first and second magnets are ring magnets. However, those having ordinary skill in the art would appreciate that the present disclosure is not limited to such a configuration for the magnets and a variety of other configurations and arrangements can be utilized while still achieving the desired operation as further described below.

Ring magnets 820, 830 may be located within annular depressions 816 of tube 810, as depicted in FIG. 8, to facilitate maintaining the locations of ring magnets 820, 830 on tube 810, or ring magnets 820, 830 may be attached to a flat outer surface 815 of tube 810. According to an exemplary embodiment, ring magnets 820, 830 may be, for example, permanent magnets or electromagnets configured to attract magnetic flow indication member 840. Second magnet 830 has a lower magnetic field strength than first magnet 820 so that flow indication member 840 is more attracted to first magnet 820, as indicated in FIG. 8. For example, if flow indication member 840 is located halfway between first magnet 820 and second magnet 830, flow indication member 840 will be more attracted to first magnet 820 and move toward first magnet 820. The attraction force between second magnet 830 and flow indication member 840 is not strong enough to overcome the attraction force between the flow indication member 840 and the first magnet 820 when the flow indication member is within a certain proximity of the first magnet 820.

When normal and desired reprocessing fluid flows through tube 810, the reprocessing fluid pressure is sufficient to move the flow indication member 840 along the direction indicated by arrow 842 toward second ring magnet 830. Tube 810 includes retention devices 814, such as meshes 814 (e.g., a wire mesh) radially protruding portions along the inner wall of tube 810, one or more pins extending into or across an inner diameter of tube, or other structure to block movement of flow indication member 840 but allow fluid flow there through so as to maintain flow indication member 840 within tube 810. Retention devices 814 may be located at positions outboard of ring magnets 820, 830, as depicted in FIG. 8. The reprocessing fluid urges flow indication member 840 along the direction indicated by arrow 842 toward second ring magnet 830. When the flow indication member 840 reaches a position within a preset proximity to second ring magnet 830, the second ring magnet 830 attracts flow indication member 840 and holds flow indication member 840 at a position (shown in dashed lines) within tube 810 proximate to second ring magnet 830.

However, in a case where fluid flow in the desired direction initially and throughout the reprocessing procedure is insufficient, the flow indication member 840 will not be moved away from its initial position held by first magnet 820. Further, if the fluid flow through the instrument becomes blocked or impeded after an initial sufficient flow of flushing fluid through the instrument, and a sufficient back flow pressure occurs based on flow in direction 844, then the flow indication mechanism 840 will be carried away from its attraction to the second magnet 830 with the fluid and move from its dashed position shown in FIG. 8 back toward its initial position. Upon a sufficient back flow pressure, the flow indication mechanism 840 eventually will be or will remain positioned within the magnetic force attraction of the first magnet 820 again and thus held in that position upon the reprocessing procedure ending. In use, priming of the flow indicator and surgical instrument with fluid can occur prior to the reprocessing procedure. In this way, an initial flow of reprocessing fluid into the flow indicator from the supply source will not trigger movement of the flow indication mechanism 840 in the direction of fluid flow. Rather, the flow indication mechanism 840 will only be triggered to change positions after the fluid has reached and is flowing through the instrument shaft. Priming can be accomplished via a syringe or other technique in a controlled manner to avoid tripping the flow indication mechanism 840.

According to an exemplary embodiment, at least a portion of tube 810 is made of a transparent or translucent material, such as a plastic or glass, so that the position of flow indication member 840 within tube 810 is observable. Therefore, if proper flow of reprocessing fluid exists during a reprocessing flushing procedure, flow indication member 840 will be located within tube 810 at a position adjacent to second ring magnet 830 when the procedure has ended, and the location of the flow indication member 840 will be observable from external to the tube 810. Similarly, if the desired reprocessing flow did not occur during the procedure, as discussed above, the location of flow indication member 840 within tube 810 at a position adjacent first magnet 820 will be observable from external to the tube 810. Thus, if proper flow of reprocessing fluid did not occur, flow indication member 840 will be located within tube 810 adjacent to first magnet 820 when the reprocessing procedure has ended because either the flow of reprocessing fluid was insufficient to force flow indication member 840 along direction 842 toward second magnet 830 and/or because a back pressure forced flow indication member 840 along direction 844 toward first magnet 820.

Flow indicator 800 also can include additional indicia to assist an observer in determining whether or not a position of flow indication member 840 indicates that a desired flow of reprocessing fluid occurred, and thus yielded a successful reprocessing of the instrument. For example, tube 810 includes indicia 832 adjacent to second magnet 830 to indicate that a proper flow has occurred, such as a colored or labeled region of tube 810 (e.g., a green region), and another, different indicia 822 adjacent to first magnet 820 to indicate that a proper flow did not occur, such as a different colored or labeled region of tube 810 (e.g., a red region). Those of ordinary skill in the art would appreciate a variety of other labels or markings that could be used as the above indicia in addition to or in lieu of colored regions, with the green and red colored regions being exemplary only.

Once a reprocessing flushing procedure has ended and flow indication member 840 is located within tube 810 at a position adjacent second magnet 830, flow indication member 840 may be returned to a position within tube 810 adjacent first magnet 820 by, for example, applying a force to flow indicator 800 to move flow indication member 840 within tube along direction 844, such as by manually tapping an end of flow indicator or running a fluid in the direction 844, with a flow sufficient to overcome the magnetic attraction force between the second magnet 830 and the flow indication member 840. In another example, at least second magnet 830 is an electromagnet and a current can be supplied (e.g., adjusted) to reverse the polarity of the magnetic field of second magnet 830, causing flow indication member 840 to repelled by second magnet 830 and to move along direction 844 toward first magnet 820. In another example, first magnet 820 is an electromagnet and a current can be supplied (e.g., adjusted) to the first magnet 820 to increase the strength of its magnetic field so that flow indication member 840 is attracted to first magnet 820, such as by a greater force than the magnetic field provided by second magnet 830.

Figure 9A:
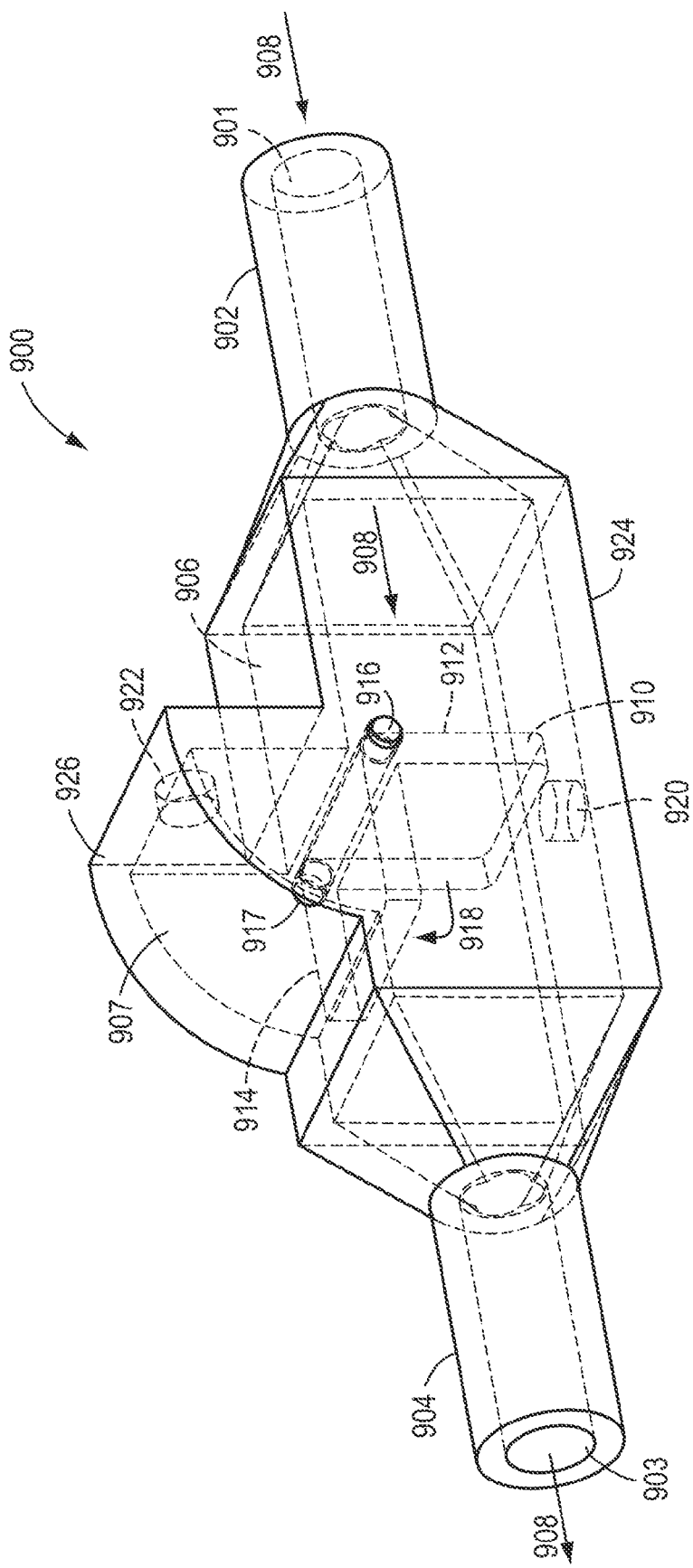
FIGS. 9A and 9B are perspective views showing an interior of a flow indicator, according to another exemplary embodiment.
Figure 9B:
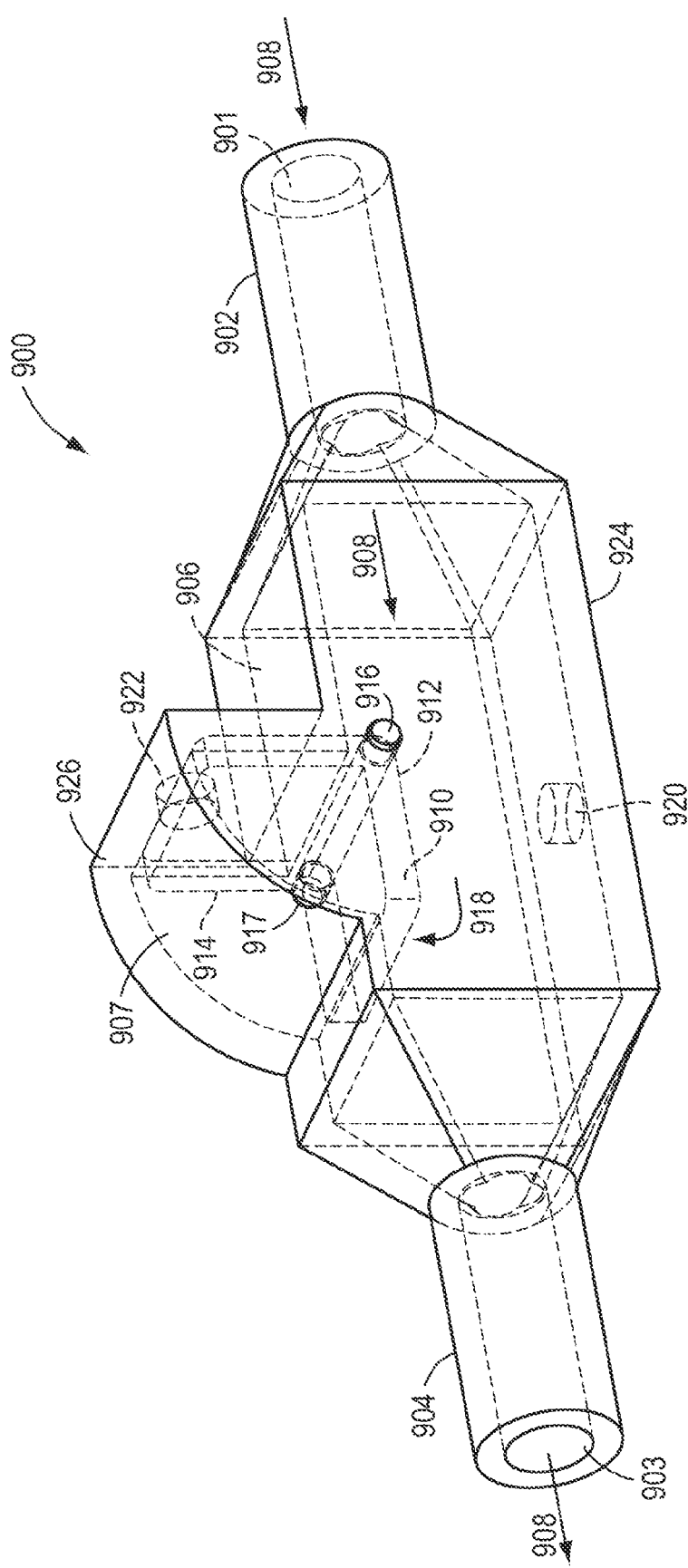

Turning to FIGS. 9A and 9B, another exemplary embodiment of a flow indicator that utilizes magnetic forces is illustrated. Flow indicator 900 includes a first tube section 902 configured to be fluidically connected to a source of reprocessing fluid (not shown) at inlet 901, and a second tube section 904 configured to be fluidically coupled to a surgical instrument at outlet 903. Thus connected, reprocessing fluid can flow through flow indicator 900 during a reprocessing flushing procedure, such as along a direction indicated by arrows 908 in FIGS. 9A and 9B. As with other embodiments, intermediate tubing may be used to couple the flow indicator 900 to a fluid supply source and a surgical instrument, respectively.

Flow indicator 900 further includes a flow housing 906 between and fluidically connected to the tube sections 902, 904 so that reprocessing fluid flows through housing 906, as indicated by arrows 908. The housing 906 houses a flow indication member 910 that is configured to change states in response to fluid flow through the housing 906, as will be described in further detail below. The flow indication member 910 includes a pivotable, paddle-like element having at least a first surface 912. As shown in one exemplary embodiment, the paddle-like element may be generally L-shaped, although those having ordinary skill in the art would appreciate other configurations that may be suitable based on the teachings of the present disclosure. As illustrated in FIG. 9A, first surface 912 is initially located within body 906 so that a flow of reprocessing fluid through flow indicator 900 is generally perpendicular to and contacts first surface 912. As a result, when flow of the reprocessing fluid is sufficient, the reprocessing fluid impinges on first surface 912 and causes flow indication member 910 to move, which indicates that the flow of reprocessing fluid was sufficient. According to an exemplary embodiment, flow indication member 910 is sized to substantially correspond to the size of the passage of the permit some of the reprocessing fluid to flow around flow indication member 910. In an exemplary embodiment, the paddle surfaces 912, 914 can have an area ranging from 50% to 95% of the area of the flow passage through the housing. For example, the area upon which the fluid flow impinges the paddle surface 912 can range from 0.5 cm² to 2 cm².

The flow indication member 910 includes a pin 916 about which flow indication member 910 pivots about an axis 917 extending along a longitudinal axis of pin 916. In particular, the flow indication member 910 pivots in the direction indicated by arrow 918 when reprocessing fluid causes flow indication member 910 to move. The housing 906 of flow indicator 900 includes a chamber 907 into which flow indication member 910 moves when the reprocessing fluid causes movement of the flow indication member 910. In particular, as illustrated in FIG. 9B, when the flow indication member 910 moves ninety degrees in direction 918, the second surface 914 moves into chamber 907 and the first surface 912 moves up to be positioned in the opening between the housing 906 and the chamber 907. Chamber 907 and/or body 906 is transparent or translucent to facilitate viewing of flow indication member 910, with a position of flow indication member 910 within chamber 907 indicating that the flow of reprocessing fluid was sufficient during a reprocessing procedure and that no blockage or hindrance causing a back pressure to prevent the flow indication mechanism 910 from moving occurred.

Flow indicator 900 also includes devices to maintain a position of flow indication member 910, whether at a position prior to a flow of reprocessing fluid occurring, or after a sufficient flow of reprocessing fluid has occurred (e.g., when flow indication member 910 has moved into chamber 907). In an exemplary embodiment, flow indication member 910 includes a magnetic material (e.g., a ferrous alloy or other magnetic material, capable of being magnetized or attracted to a magnet, familiar to one of ordinary skill in the art), which may be encased in another material, such as a plastic, to protect the magnetic material from the reprocessing fluid. To hold flow indication member 910 in the initial position prior to a flow of reprocessing fluid, depicted in FIG. 9A, a first magnet 920 may be located within a wall 924 of flow indicator 900 that forms housing body 906. Due to its inclusion of magnetic material, flow indication member 910, and in particular first surface 912, is attracted to first magnet 920 and held in the position depicted in FIG. 9 until a sufficient flow of reprocessing fluid flows through flow indicator, as indicated by arrows 908, which contacts flow indication member 910, overcomes the force between first magnet 920 and flow indication member 910, and moves flow indication member 910 along the direction indicated by arrow 918 into chamber 907 (e.g., pivots flow indication member 910 ninety degrees in direction 918 into the position depicted in FIG. 9B). A second magnet 922 is included in flow indicator 900, such as within a wall 926 of chamber 907, to attract flow indication member 910, and in particular second surface portion 914, and hold flow indication member 910 at a position within chamber 907 adjacent to second magnet 922 so that when a reprocessing procedure has concluded, the flow indication member 910 may be observed within chamber 907, which indicates that a sufficient flow of reprocessing fluid occurred during the reprocessing procedure. Accordingly, if the flow indication member 910 is not observable in the chamber 907 this signifies that insufficient flow occurred during reprocessing. In a manner similar to the embodiment of FIG. 8, the magnet 920 may have a stronger magnetic force acting on the flow indication mechanism 910 than magnet 922 when the flow indication mechanism 910 is pivoted half way between the first shaft and the second shaft.

In an exemplary embodiment of the operation of the flow indicator 900 of FIGS. 9A and 9B, prior to beginning an instrument reprocessing flushing procedure, the flow indicator 900 can be connected to the instrument. For example, second tube section 904 can be fluidically coupled to the instrument as described above. Prior to connecting first tube section 902 to a fluid supply source, the instrument and the indicator can be primed with fluid. Such priming is useful to avoid prematurely tripping the flow indication mechanism 910 upon initially flowing the reprocessing flushing fluid through first tube section 902, housing 906, second tube section 904, and into the instrument shaft. Priming can be accomplished via a syringe or other suitable technique to introduce fluid to the instrument and the flow indicator in a relatively controlled manner so as to avoid pivoting the flow indication member 910 from its initial position within the housing 906.

After completion of priming, the flow indicator can be fluidically coupled to the fluid supply source (whether from a manual source or an automated machine washer), and the reprocessing flushing procedure can begin. If a blockage exists so as to prevent or hinder fluid from flowing through the instrument, a back pressure will occur upon beginning the flushing procedure, thereby resulting in an insufficient fluid pressure acing on face 912 of the flow indication member 910. Accordingly, flow indication member 910 will maintain its initial position depicted in solid in FIG. 9A. Upon completion of the reprocessing flushing procedure, therefore, the untripped flow indication member 910 will not have moved and surface 914 will not have moved into chamber 907. On the other hand if the instrument has no blockages or impediments to fluid flow, eventually the fluid will flow into the instrument shaft and thus a sufficient pressure will be exerted to trip the pivoting and rotation of the 910 to the second position with the surface 914 shown in chamber 907, as shown in FIG. 9B.

Once a reprocessing procedure has ended, flow indicator 910 may be returned to the position depicted in FIG. 9A by, for example, applying a force to flow indicator 900 to move flow indication member 910 in a direction opposite to the direction indicated by arrow 918 (e.g., by manually tapping flow indicator). In another example, at least second magnet 922 is an electromagnet and the current supplied to second magnet 922 can be changed to reverse the polarity of the magnetic field of second magnet 922, causing second magnet 922 to repel flow indication member 910 so flow indication member 910 moves along a direction opposite to the direction indicated by arrow 918 toward first magnet 920.

Figure 10:
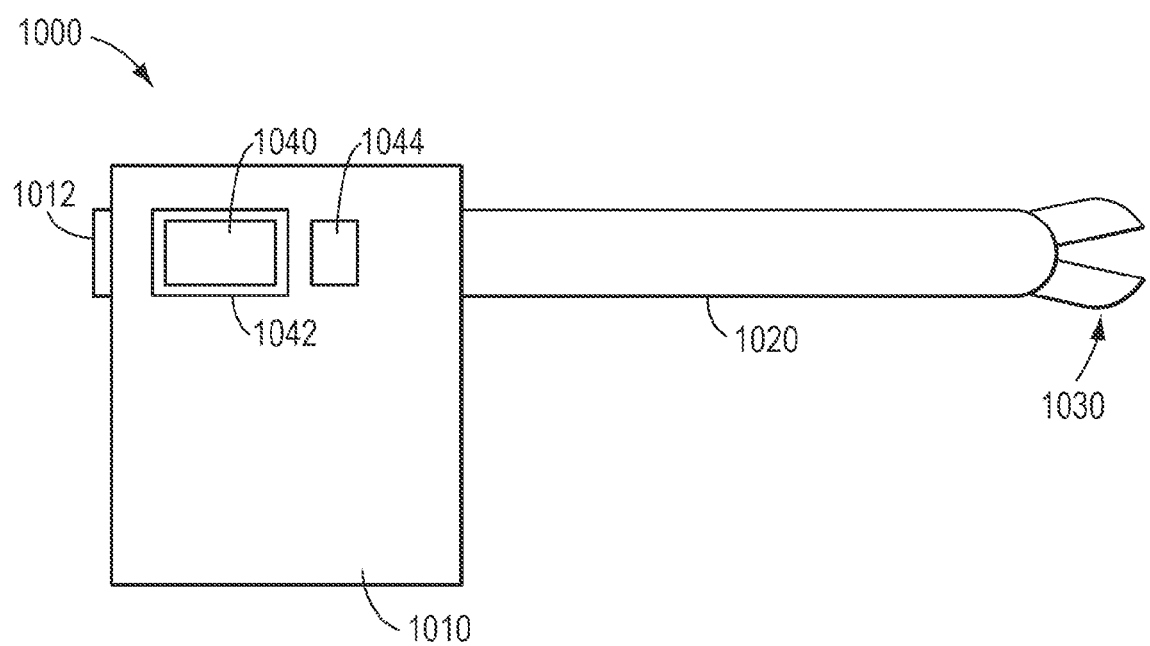
FIG. 10 is a schematic side view of a surgical instrument including an internal flow indicator, according to an exemplary embodiment.

The various exemplary embodiments of flow indicators discussed above have been described as separate components that are fluidically connected to a surgical instrument during a reprocessing procedure. The present disclosure further contemplates surgical instruments that include a flow indicator as an on-board, built-in component of the surgical instrument itself. Turning to FIG. 10, a side view of a surgical instrument 1000 is schematically depicted. Surgical instrument 1000 includes a force transmission mechanism 1010, a shaft 1020, and an end effector 1030. Surgical instrument 1000 may include other components, such as those, for example, described above for the exemplary embodiment of FIG. 2.

Surgical instrument 1000 includes a flow indicator 1040, which may be configured as any of the various exemplary embodiments of flow indicators described herein. Flow indicator 1040 can be fluidically connected to a supply of reprocessing fluid flowing through surgical instrument, such as a supply of reprocessing fluid connector to port 1012, as described above with regard to the exemplary embodiment of FIG. 2. For example, an inlet (not shown in FIG. 10) of flow indicator 1040 is fluidically connected to at least one of port 1012 while an outlet (not shown in FIG. 10) of flow indicator 1040 is fluidically connected to the interior of shaft 1020. Flow indicator 1040 is located, for example, within force transmission mechanism 1010, which may include a window (e.g., a transparent portion of force transmission mechanism 1010) to facilitate viewing of flow indicator 1040, although flow indicator 1040 may be located within other portions of surgical instrument 1000, such as, for example shaft 1020. Surgical instrument 1000 may further include an actuator 1044 for flow indicator 1040, such as a mechanism to return flow indicator to an initial state (e.g., via mechanical or non-mechanical means, such as via an electromagnet) prior to a flow of reprocessing fluid flowing through flow indicator 1040.

In various exemplary embodiments wherein a flow indication mechanism is positioned within the main fluid path of reprocessing fluid through the flow indicator in order to perform a reprocessing flushing of a surgical instrument, the portion of the flow indication mechanism that is within the flow of the fluid can be sized such that it permits flow around the portion during normal flow of the reprocessing fluid, but will be subject to pressure forces when it is desired to be used to indicate a back flow pressure occurred. Accordingly, such flow indication mechanisms may be configured to minimize space requirements within the instrument.

The present disclosure contemplates modifying flow indicators described herein for various surgical instruments. For instance, surgical instruments can have different sizes and/or configurations, which affect how reprocessing fluid flows through a surgical instrument and the pressure and flow rate of the reprocessing fluid when flowing through an instrument. In view of this, a flow indicator can be tuned to be used with a particular type of surgical instrument so the flow indicator will provide an accurate indication of fluid flow through the instrument. For example, an indicator can be tuned for use with surgical instruments having a shaft diameter ranging from 3 mm to 12 mm of, for example, about 5 mm, or about 8 mm.

According to an exemplary embodiment, flow indicators may be tuned to indicate a low flow rate for a particular type of instrument when the flow rate has dropped to, or below, a threshold flow rate (e.g., a baseline flow rate). The threshold flow rate may be, for example, a flow rate of reprocessing fluid through a particular type of instrument (e.g., instrument of a particular shaft diameter) without obstructions to the flow of reprocessing fluid, such as when a cleaning operation initially begins. For a shaft having a diameter of about 5 mm, a flow indicator may be configured to indicate an insufficient flow when the flow rate is at 25% or less of the threshold flow rate. For a shaft having a diameter of about 8 mm, the flow indicator may be configured to indicate a back flow when the flow rate is at 70% or less of the threshold flow rate.

Tuning can be accomplished by measuring the flow rate and back pressure when an unblocked instrument is attached to a flow indicator. These values can be used to set the "Normal" or "Green" (sufficient flow) range of the indicator. Subsequently, an instrument of the same type is used with a blocked flush tube, which can be accomplished, for example, by introducing foreign material such as sand or the like into the flush lumen. The blocked instrument is attached and the higher back pressure and lowered flow are noted as a "Failing" or "Red" (insufficient flow) indicator, or any other suitable indicator to indicate to an observer that the fluid flushing of the instrument likely was not successful. According to an exemplary embodiment, a flow indicator is configured to indicate a complete blockage for fluid flow through an instrument. Thus, an indicator may be configured to either indicate that no flow has occurred (e.g., flow has been blocked), meaning that the threshold flow rate is zero. Alternatively, flow indicators of various exemplary embodiments can be configured to indicate that an amount of flow greater than no flow (i.e., complete blockage) has occurred, but that the flow was insufficient during the reprocessing to be able to reliably ensure that successful reprocessing occurred.

According to an exemplary embodiment, flow indicators can be tuned according to the machine washer (e.g., machine washer 300 in FIG. 3) the flow indicator will be used with. Machine washers may vary in the amount of reprocessing fluid pressure delivered, such as according to the power of a pump (e.g., pump 310 in FIG. 3) used by a machine washer. Machine washer pumps may deliver a pressure ranging from, for example, about 30 psi to about 60 psi. Therefore, a flow indicator can be tuned according to the pump psi, such as by having a threshold flow rate selected in view of the pressure supplied by the machine washer pump. For example, a threshold flowrate resulting in 25% or less of a pressure of about 30 psi to about 60 psi (depending on the machine washer) for a 5 mm diameter instrument, or, for example, a threshold flow rate resulting in 70% or less of a pressure of about 30 psi to about 60 psi for an 8 mm diameter instrument. According to an exemplary embodiment, a flow indicator configured to indicate a complete blockage for fluid flow through an instrument is tuned according to the machine washer the flow indicator will be used. For example, a flow indicator configured to indicate a complete blockage is tuned to indicate a complete blockage when a back pressure of about 30 psi occurs for a washer that delivers a reprocessing fluid pressure of about 30 psi. In another example, a flow indicator configured to indicate a complete blockage is tuned to indicate a complete blockage when a back pressure of about 60 psi occurs for a washer that delivers a reprocessing fluid pressure of about 60 psi.

Although the flow indicators, surgical instruments, and methods have been described herein with reference to teleoperated surgical systems, the present disclosure contemplates non-teleoperated surgical instruments, such as, for example, manually operated surgical instruments (e.g., hand held surgical instruments), which may be used with the various exemplary embodiments described herein.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

The nature of information depicted in the figures and described herein is exemplary. Those persons having skilled in the art would appreciate modifications to the flow indicators and instruments can be made, such as for example, This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

It is to be understood that the particular examples and embodiments set forth herein are nonlimiting, and modifications to structure, dimensions, materials, and methodologies may be made without departing from the scope of the present disclosure and claims including equivalents.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents.

What is claimed is:

1. A surgical instrument flow indicator, comprising:
a body defining a flow passage comprising an inlet and an outlet, wherein the inlet is configured to be fluidically coupled to a fluid supply source, and wherein the outlet is configured to be fluidically coupled to a surgical instrument; and
a flow indication mechanism fluidically coupled with the flow passage, the flow indication mechanism being transitionable from a first state to a second state in response to a threshold force exerted on the flow indication mechanism by a fluid flowing through the flow passage,
wherein in the second state, the flow indication mechanism has an arrangement indicating to an observer that the flow indication mechanism transitioned from the first state to the second state.

2. The flow indicator of claim 1, wherein the inlet is configured to be coupled to a reprocessing fluid supply source of a surgical instrument reprocessing machine washer.

3. The flow indicator of claim 1, wherein the flow indication mechanism comprises a piston assembly, the piston assembly comprising a piston head in a piston chamber.

4. The flow indicator of claim 3, wherein the piston chamber forms part of the flow passage.

5. The flow indicator of claim 3, further comprising a shaft extending from the piston head, through an opening at an end of the piston chamber, to an exterior of the flow indicator.

6. The flow indicator of claim 5, wherein the shaft is hollow and forms part of the flow passage, the shaft including the inlet.

7. The flow indicator of claim 5, wherein the flow indication mechanism further comprises a biasing device positioned to exert a biasing force to retain the piston head in a first position in the first state of the flow indication mechanism, the biasing force being less than the threshold force.

8. The flow indicator of claim 5, wherein the flow indication mechanism further comprises an anti-backlash mechanism configured to maintain a position of the flow indication mechanism after transition of the flow indication mechanism to the second state.

9. The flow indicator of claim 8, wherein the anti-backlash mechanism comprises a plate pivotably coupled to an end of the piston chamber at which the opening is located, the plate comprising an aperture through which the shaft extends, an angular orientation of the aperture being altered based on pivoting movement of the plate.

10. The flow indicator of claim 9, wherein the plate frictionally engages the shaft in the second state, the frictional engagement being sufficient to maintain a position of the shaft and piston head in the second state against the biasing force exerted on the piston head by the biasing device.

11. The flow indicator of claim 5, further comprising indicia on the shaft, the indicia indicating to an observer a level of threshold force exerted on the flow indication mechanism during transition of the flow indication mechanism from the first state to the second state.

12. The flow indicator of claim 1, wherein the flow indication mechanism further comprises an anti-backlash mechanism configured to maintain a position of the flow indication mechanism after transition of the flow indication mechanism to the second state.

13. The flow indicator of claim 1, wherein the flow indication mechanism comprises a magnetically attractive element located within the flow passage, the magnetically attractive element being configured to move from a first position in the first state of the flow indication mechanism to a second position in the second state of the flow indication mechanism.

14. The flow indicator of claim 13, further comprising a first magnet and a second magnet spaced apart from one another along the flow passage, wherein the magnetically attractive element is retained in the first position by the first magnet and in the second position by the second magnet.

15. The flow indicator of claim 1, wherein the threshold force is associated with a backpressure of reprocessing fluid during reprocessing fluid flowing from the inlet to the outlet of the flow passage.

16. A flow indicator for use during reprocessing of a surgical instrument, the flow indicator comprising:
a body defining a flow passage comprising an inlet and an outlet, wherein the inlet is configured to be fluidically coupled to a fluid supply source, and wherein the outlet is configured to be fluidically coupled to the surgical instrument; and
a flow indication mechanism movable between a first position and a second position;
a first retention mechanism positioned and configured to exert a first retention force on the flow indication mechanism to retain the flow indication mechanism in the first position, the first retention force being less than a threshold force acting in a direction to move the flow indication mechanism to the second position; and
a second retention mechanism positioned and configured to exert a second retention force on the flow indication mechanism to retain the flow indication mechanism in the second position.

17. The flow indictor of claim 16, wherein:
the first retention force and the second retention force are magnetic attraction forces, and
the flow indication mechanism comprises a magnetically attractive element disposed in the flow passage.

18. The flow indicator of claim 17, wherein:
the flow indication mechanism comprises: a piston head in a piston chamber in flow communication with the flow passage;
a shaft extending from the piston head through an opening at an end of the piston chamber and to an exterior of the flow indicator;
the first retention mechanism comprises a spring extending between the piston head and the end of the piston chamber; and
the second retention mechanism comprises an anti-backlash plate coupled to the end of the piston chamber, the shaft extending through the anti-backlash plate.

19. A method of reprocessing a surgical instrument, the method comprising:
fluidically coupling a flow indicator between a reprocessing fluid supply source and a surgical instrument; and
flushing portions of the surgical instrument by flowing a reprocessing fluid from the fluid supply source through the flow indicator and to the portions of the surgical instrument;
wherein the flow indicator has a first state prior to the reprocessing fluid flowing through the flow indicator in a direction from the fluid supply source to the surgical instrument; and
wherein, on the condition that a sufficient backflow pressure of reprocessing fluid occurs during the flowing, the flow indicator transitions from the first state to a second state, the flow indicator remaining in the second state after the flow indicator transitions from the first state to a second state and after the flowing of the reprocessing fluid.

20. The method of claim 19, wherein in the second state, the flow indicator indicates to an observer that the flow indicator transitioned from the first state to the second state.

21. The method of claim 19, wherein flowing the reprocessing fluid from the fluid supply source comprises flowing the reprocessing fluid during an automated reprocessing procedure, the automated reprocessing procedure using a reprocessing machine washer.

22. A surgical instrument reprocessing system, the system comprising:
a machine washer comprising a reprocessing fluid supply source; and
a flow indicator body comprising:
an inlet configured to be fluidically coupled to the machine washer reprocessing fluid supply source;
an outlet configured to be fluidically coupled to a surgical instrument so as to flow reprocessing fluid from the machine washer reprocessing fluid supply source through an interior of a shaft of the surgical instrument;
a flow passage extending from the inlet to the outlet; and
a flow indication mechanism fluidically coupled with the flow passage, the flow indication mechanism being transitionable from a first state to a second state in response to a threshold force exerted on the flow indication mechanism by the reprocessing fluid flowing through the flow passage,
wherein in the second state, the flow indication mechanism has an arrangement indicating to an observer of the flow indicator that the flow indication mechanism transitioned from the first state to the second state.

* * * * *